(12) United States Patent
Saul et al.

(10) Patent No.: US 8,309,367 B2
(45) Date of Patent: Nov. 13, 2012

(54) MICROWAVE MICROFLUIDICS

(75) Inventors: Richard Saul, Gaithersburg, MD (US); Mark T. Martin, Rockville, MD (US)

(73) Assignee: Mirari Biosciences, Inc., Rockville, MD (US)

( * ) Notice: Subject to any disclaimer, the term of this patent is extended or adjusted under 35 U.S.C. 154(b) by 1558 days.

(21) Appl. No.: 11/105,460

(22) Filed: Apr. 14, 2005

(65) Prior Publication Data

US 2005/0191708 A1    Sep. 1, 2005

Related U.S. Application Data

(63) Continuation-in-part of application No. 10/234,092, filed on Sep. 5, 2002, now Pat. No. 7,348,182, which is a continuation-in-part of application No. 09/968,517, filed on Oct. 2, 2001, now Pat. No. 7,351,590.

(60) Provisional application No. 60/237,192, filed on Oct. 3, 2000.

(51) Int. Cl.
*G01N 33/53* (2006.01)

(52) U.S. Cl. ............ 436/518; 436/173; 436/51; 436/50; 436/149; 436/806

(58) Field of Classification Search .................. 436/518, 436/173, 50, 51, 806, 149
See application file for complete search history.

(56) References Cited

U.S. PATENT DOCUMENTS

| 3,455,842 A | 7/1969 | Cornelius et al. |
| 3,839,175 A | 10/1974 | Keyes |
| 4,221,680 A * | 9/1980 | Hardwick et al. ............ 588/11 |
| 4,340,672 A | 7/1982 | Kondo et al. |
| 4,575,485 A | 3/1986 | Sizto et al. |
| 4,683,195 A | 7/1987 | Mullis et al. |
| 4,683,202 A | 7/1987 | Mullis et al. |
| 4,745,077 A | 5/1988 | Holian et al. |
| 4,822,492 A | 4/1989 | Chao et al. |
| 4,822,566 A | 4/1989 | Newman |
| 4,880,752 A | 11/1989 | Keck et al. |
| 5,285,040 A | 2/1994 | Brandberg et al. |
| 5,350,686 A | 9/1994 | Jhingan et al. |

(Continued)

FOREIGN PATENT DOCUMENTS

EP    0 487 091 A2    5/1992

(Continued)

OTHER PUBLICATIONS

Bekkum et al, "Supported Zeolite Systems and Applications," Studies in Surface Science and Catalysis, Elsevier Science B.V., Amsterdam, NL, vol. 85, pp. 509-542 (1994).

(Continued)

*Primary Examiner* — Mark Shibuya
*Assistant Examiner* — Pensee Do
(74) *Attorney, Agent, or Firm* — Jenkins, Wilson, Taylor & Hunt, P.A.

(57) ABSTRACT

The present invention concerns a novel means by which liquids can be moved or mixed. Microwaves strike and heat materials that are highly susceptible to microwave heating. The susceptible materials are on, within, or near materials that melt or change shape in response to temperature increases. Upon microwave irradiation, these materials change shape (e.g., shrink or melt), causing the movement of liquids. The invention is important in many microfluidics applications, especially in biomedical analysis, where it is valuable to be able to move small volumes of liquids (e.g., on a microarray chip).

15 Claims, 6 Drawing Sheets

1. microwave irradiation

2. Composite consisting of;
   (a) material that is highly susceptible to microwave heating, and
   (b) material that physically transforms upon heating.

3. A fluid close enough to the heat-transformable material (b) to be physically affected by physical changes in said material.

U.S. PATENT DOCUMENTS

| | | | |
|---|---|---|---|
| 5,403,747 | A | 4/1995 | Akins et al. |
| 5,427,779 | A | 6/1995 | Elsner et al. |
| 5,451,428 | A | 9/1995 | Rupp |
| 5,478,748 | A | 12/1995 | Akins et al. |
| 5,496,701 | A | 3/1996 | Pollard-Knight |
| 5,689,008 | A | 11/1997 | Satyapal et al. |
| 5,767,470 | A | 6/1998 | Cha |
| 5,780,578 | A | 7/1998 | Mashelkar et al. |
| 5,846,843 | A | 12/1998 | Simon |
| 5,869,349 | A | 2/1999 | Lin et al. |
| 5,911,941 | A | 6/1999 | Rokhvarger et al. |
| 5,922,537 | A | 7/1999 | Ewart et al. |
| 5,939,614 | A | 8/1999 | Walters et al. |
| 5,985,356 | A | 11/1999 | Schultz et al. |
| 6,004,534 | A | 12/1999 | Langer et al. |
| 6,011,247 | A | 1/2000 | Grillo et al. |
| 6,029,498 | A | 2/2000 | Walters et al. |
| 6,034,775 | A | 3/2000 | McFarland et al. |
| 6,093,302 | A | 7/2000 | Montgomery |
| 6,099,864 | A | 8/2000 | Morrison et al. |
| 6,140,045 | A | 10/2000 | Wohlstadter et al. |
| 6,159,681 | A | 12/2000 | Zebala |
| 6,180,415 | B1 | 1/2001 | Schultz et al. |
| 6,235,241 | B1 | 5/2001 | Catt et al. |
| 6,255,477 | B1 | 7/2001 | Kleiber et al. |
| 6,316,153 | B1 * | 11/2001 | Goodman et al. ............... 430/8 |
| 6,355,491 | B1 | 3/2002 | Zhou et al. |
| 6,413,783 | B1 | 7/2002 | Wohlstadter et al. |
| 6,630,358 | B1 | 10/2003 | Wagner et al. |
| 7,348,182 | B2 | 3/2008 | Martin et al. |
| 7,351,590 | B2 | 4/2008 | Martin |
| 7,718,445 | B2 | 5/2010 | Martin |
| 2002/0197645 | A1 * | 12/2002 | Martin ........................ 435/7.1 |
| 2003/0082633 | A1 | 5/2003 | Martin |
| 2004/0209303 | A1 | 10/2004 | Martin |
| 2008/0248489 | A1 | 10/2008 | Martin |

FOREIGN PATENT DOCUMENTS

| | | |
|---|---|---|
| GB | 1363526 | 8/1974 |
| JP | S64-002608 | 1/1989 |
| JP | H03-238895 | 10/1991 |
| JP | H04-260472 | 9/1992 |
| JP | H06-043161 | 2/1994 |
| JP | H08-105892 | 4/1996 |
| JP | H09-255365 | 9/1997 |
| JP | H09-297138 | 11/1997 |
| WO | WO02/29076 | 4/2002 |

OTHER PUBLICATIONS

Cornelis & Laszlo, "Oxidation of Alcohols by Clay-Supported Iron (III) Nitrate; A New Efficient Oxidizing Agent," Synthesis, vol. 1980, pp. 849-850 (Oct. 1980).
Office Communication corresponding to U.S. Appl. No. 12/059,427 dated Dec. 12, 2008.
Office Communication corresponding to the European Patent Application No. 01979344.7-2404 dated Feb. 15, 2007.
Communication Pursuant to Article 94(3) EPC corresponding to European Patent Application No. 01 979 344.7-2404 dated Feb. 17, 2009.
Official Action corresponding to Japanese Patent Application No. 2002-532645 dated Mar. 25, 2008.
Official Action corresponding to an Australian Patent Application No. 2003254187 dated Jun. 2, 2008.
Official Action corresponding to Japanese Patent Application No. 2004-534253 dated Oct. 7, 2008.
Office Communication corresponding to U.S. Appl. No. 10/842,512 dated Oct. 14, 2009.
Notice of Allowance corresponding to U.S. Appl. No. 12/059,427 dated Dec. 29, 2009.
Issued Patent corresponding to Australian Patent Application No. 2003254187 dated Oct. 29, 2009.
Adeyeye and Price, Pharm. Res., vol. 8, pp. 1377-1383 (1991).
Basu and Basu, Liposome Methods and Protocols, Humana Press, Totowa, NJ, pp. 3-16 (2002).
Becker and Gartner, Electrophoresis, vol. 21, pp. 12-26 (2000).
Beebe et al, Annu. Rev. Biomed., vol. 4, pp. 261-286 (2002).
Blackwell, H. E., Org. Biomol. Chem., vol. 1, pp. 1251-1255 (2003).
Bradley, D., "The Nuke's the Thing for Synthesis," Modern Drug Discovery, vol. 4, No. 8, pp. 32-36 (2001).
Burtsoff, Modern Drug Discovery, vol. 7, pp. 55-56 (2004).
Cahnman, H., "Infrared: How Does It Work?" downloaded Jul. 25, 2006 from http://www.cassosolar.com/sales/how_it_works.htm.
Chen and Chen, Electrophoresis, vol. 21, pp. 165-170 (2000).
Committee on Microwave Processing of Materials, National Materials-Advisory Board, Commission on Engineering and Technical Systems, and National Research Council (1994) Microwave Processing of Materials. Washington, DC, National Academy Press.
Constans, A., The Scientist, pp. 43-45 (Nov. 2003).
Donbrow, "Microcapsules and Nanoparticles in Medicine and Pharmacy," CRC Press, Boca Raton, FL, pp. 1-14 (1991).
Drummond et al., Pharm. Rev., vol. 51, pp. 691-743 (1999).
Duzgunes, N., Methods Enzymol., vol. 367, pp. 99-110 (2003).
Duzgunes, N., Methods Enzymol., vol. 373, pp. 260-277 (2004).
Fermer et al., Eur. J. Pharm. Sci., vol. 18, pp. 129-132 (2003).
Fitzgerald, D. A., The Scientist, vol. 16, pp. 40-42 (2002).
Fleischer, C.T. & Boos, K.-S. (2001) American Laboratory, May 30, 20-25.
Fong et al., 79, pp. 271-276 (2002).
Futaki, S., "Peptide Ion Channels: Design and Creation of Function," Biopolymers (Peptide Science), vol. 47, pp. 75-81 (1998).
Giordano et al., Anal. Biochem., vol. 291, pp. 124-132 (2001).
Gloffke, The Scientist, vol. 17, No. 8, pp. 41-43 (2003).
Gregoriadis, G., "Liposome Technology, vol. III, Targeted Drug Delivery and Biological Interaction," CRC Press, Boca Raton, FL, pp. 137-155 (1983).
Gregoriadis, G., Liposome Technology, vol. I, Preparation of Liposomes, CRC Press, Boca Raton, FL, pp . 1-18 (1983).
Hansen and Quake, Curr. Opin. Struct. Biol., vol. 13, pp. 538-544 (2003).
Hjerpe et al., 20, 388-396 (1988).
Hoffman, A. S., Clin. Chem., vol. 46, pp. 1478-1486 (2000).
Jain et al., Anal. Biochem., vol. 311, pp. 84-86 (2002).
Jansen et al., "Preparation of Coatings of Molecular Sieve Crystals for Catalysis and Separation," Studies in Surface Science and Catalysis, Elsevier Science B.V., Amsterdam, NL, vol. 85, pp. 215-250 (1994).
Jeong and Gutowska, Trends Biotechnol., vol. 20, pp. 305-311 (2002).
Kok and Boon, Histochem. J., vol. 22, pp. 381-388 (1990).
Kono, K., Adv. Drug Deliv. Rev., vol. 53, pp. 307-319 (2001).
Kreider, K.G., "Thin Film Thermocouples for High Temperature Measurement," NIST, Springfield, VA (1989).
Leong and Milios, J. Pathol., vol. 148, pp. 183-187 (1986).
Lesney, M. S., Modern Drug Discovery, vol. 5, pp. 37-41 (2002).
Maugard et al., Biotechnol. Lett., vol. 25, 623-629 (2003).
McDonald et al., Electrophoresis, vol. 21, pp. 27-40 (2000).
McPherson and Moller, "PCR," Bios Scientific Publishers, Oxford, UK (2000).
Microwave Processing of Materials V. in Mat. Res. Soc. Symp. Proc. 430, Iskander, MF et al., eds. (1996).
Nataranjan et al., Bioelectromagnetics, vol. 23, pp. 271-277 (2002).
Newton and Graham, "PCR," Springer-Verlag, New York (1997).
Notice of Allowance corresponding to U.S. Appl. No. 09/968,517 (U.S. Patent No. 7,351,590) dated Jan. 16, 2008.
Notice of Allowance corresponding to U.S. Appl. No. 09/968,517 (U.S. Patent No. 7,351,590) dated Oct. 5, 2007.
Notice of Allowance corresponding to U.S. Appl. No. 10/234,092 (U.S. Patent No. 7,348,182) dated Oct. 2, 2007.
Notice of Allowance corresponding to U.S. Appl. No. 10/234,092 (U.S. Patent No. 7,348,182) dated Jan. 16, 2008.
Office Communication corresponding to U.S. Appl. No. 09/968,517 (U.S. Patent No. 7,351,590) dated Apr. 5, 2005.
Office Communication corresponding to U.S. Appl. No. 09/968,517 (U.S. Patent No. 7,351,590) dated Jan. 9, 2006.
Office Communication corresponding to U.S. Appl. No. 09/968,517 (U.S. Patent No. 7,351,590) dated Nov. 3, 2006.

Office Communication corresponding to U.S. Appl. No. 09/968,517 (U.S. Patent No. 7,351,590) dated May 15, 2007.
Office Communication corresponding to U.S. Appl. No. 10/234,092 (U.S. Patent No. 7,348,182) dated Nov. 9, 2006.
Office Communication corresponding to U.S. Appl. No. 10/234,092 (U.S. Patent No. 7,348,182) dated May 15, 2007.
Office Communication corresponding to U.S. Appl. No. 10/842,512 dated Oct. 19, 2005.
Office Communication corresponding to U.S. Appl. No. 10/842,512 dated Jan. 8, 2007.
Office Communication corresponding to U.S. Appl. No. 10/842,512 dated Oct. 3, 2007.
Office Communication corresponding to U.S. Appl. No. 10/842,512 dated Jan. 24, 2008.
Office Communication corresponding to U.S. Appl. No. 12/059,427 dated Sep. 17, 2009.
Official Communication corresponding to Japanese Patent Application No. 2002-532645 dated Jun. 1, 2010.
Official Communication corresponding to Japanese Patent Application No. 2004-534253 dated Jun. 1, 2010.
Official Communication corresponding to Canadian Patent Application No. 2,498,005 dated May 13, 2010.
Ostro, M. J., "Liposome. From Biophysics to Therapeutics," Marcel Dekker, New York, pp. 297-298 (1987).
Roper et al., vol. 75, pp. 4711-4717 (2003).
Roy and Gupta, Chemistry and Biology, vol. 10, pp. 1161-1171 (2003).
Saaristo et al., "Mechanisms of angiogenesis and their use in the inhibition of tumor growth and metastasis ," Oncogene, vol. 19, pp. 6122-6129 (2000).
Slap, S. E., Am. Biotechnol. Laboratory, Nov., 40 (2003).
Stillman and Tonkinson, BioTechniques, vol. 29, p. 630 (2000).
Surrmeijer et al., Histochem. J., vol. 22, pp. 341-346 (1990).
Terabe, S., Anal. Chem., vol. 76, pp. 240A-246A (2004).
Torchilin and Weissig, Liposomes. A Practical Approach, $2^{nd}$ Ed., Oxford Univ. Press, Oxford UK, pp. 3-29 (2004).
Van de Kant et al., Histochem. J., vol. 20, pp. 335-340 (1988).
Van den Brink et al., Histochem. J., vol. 22, pp. 327-334 (1990).
Xiang, X., "Combinatorial materials synthesis and high-throughput screening: An integrated materials chip approach to mapping phase diagrams and discovery and optimization of functional materials," Biotechnol. Bioeng., vol. 58, pp. 227-241 (1998).
Abati et al. *Looking forward in diagnostic pathology. Cancer*, vol. 78, (1996), pp. 1-3.
Baziard et al. Cross-linkingunder microwaves (2.45 GHz) of aluminum powder-epoxy resin composites I. Electrical power dependence. *European Polymer Journal*, vol. 24. (1988), p. 873.
Boon et al. in "Microwave cookbook of pathology." Coulomb Press, Leiden. 1989. pp. 1-219.
Boon et al. in "Microwave cookbook of pathology." Coulomb Press, Leiden. 1989. p. 17.
Borchart et al. Synthetic receptor binding elucidated with an encoded combinatatorial library. *Journal of American Chemical Society*, vol. 116, (1994), p. 373.
Borman, S. Combinatorial chemistry. *Chemical and Engineering News*, (Aug. 21, 2001), pp. 49-58.
Bose et al. MORE chermistry in microwave. *Chemtech*, vol. 27, No. 9, (1997), pp. 18-25.
Bowie et al. Analytical applications of liquid phase chemiluminescence reactions—a review. *Journal of bioluminescence and chemiluminescence*, vol. 11, (1996), pp. 61-90.
Bram et al. Alkylation of potassium acetate in "Dry Media" thermal activation in commercial microwave ovens. *Tetrahedron*, vol. 46, (1990), p. 5167.
Bram et al. in: "Anthraquinone microwave-induced synthesis in dry media in domestic ovens." Chem. Ind. 1991. p. 396.
Breslow et al. Optimization of metallocene substrates for beta-cyclodextrin reactions. *Journal of American Chemical Society*, vol. 105, (1983), p. 2739.
Buffler et al. Microwave processing of materials. *Materials Research Society Symposium Proceedings*, vol. 430, (1996), p. 85.

Burow et al. Molecular imprinting: Synthesis of polymer particles with antibody-like binding characteristics for glucose oxidase. *Biochemical and Biophysical Research Communications*, vol. 227, (1996), p. 419.
Bystrom et al. Selective reduction of steroid 3- and 17-ketones using LiAlH4 activated template polymers. *Journal of the American Chemical Society*, vol. 115, (1993), p. 2081.
Cooper, C.S. Applications of microarray technology in breast cancer research. *Breast Cancer Research*, vol. 3, (2001), pp. 158-175.
Dai et al. Imprint Coating: a novel synthesis of selective functionalized ordered mesoporous sorbents. *Angewandte Chemie International Edition*, vol. 38, (1999), p. 1235.
Dickert et al. Molecularly imprinted polymers for optichemical sensors. *Advanced Materials*, vol. 8, (1996), p. 987.
Dolle et al. Comprehensive survey of combinatorial library synthesis: 1999. *Journal of Combinatorial Chemistry*, vol. 2, (2000), pp. 383-433.
Draghici et al. Experimental design, analysis of variance and slide quality assessment in gene expression arrays *Current Opinion in Drug Discovery and Development*, vol. 4, (2001), pp. 332-337.
Fodor et al. Multiplexed biochemical assays with biological chips. *Nature*, vol. 3, (1993), pp. 555-556.
Folkman, J. Angiogenesis and angiogenesis inhibition: an overview. *EXS*, vol. 79, (1997), pp. 1-8.
Freeman et al. Quantitative RT-PCR: Pitfalls and potential. *BioTechniques*, vol. 26, (1985), pp. 112-125.
Gabriel et al. Dielectric parameters relevant to microwave dielectric heating. *Chemical Society Reviews*, vol. 27, (1998), pp. 213-224.
Gallop et al. Applications of combinatorial technologies to drug discovery. 1. Background and peptide combinatorial libraries. *Journal of Medicinal Chemistry*, vol. 37, No. 9, (1994), pp. 1233-1251.
Glad et al. Use of Silane monomers for molecular imprinting and enzyme entrapment in polysiloxane-coated porous silica. *Journal of Chromatography*, vol. 347, (1985), p. 11.
Gordon et al. Applications of combinatorial technologies to drug discovery. 2. Combinatorial organic synthesis, Library Screening Strategies and Future directions. *Journal of Medicinal Chemistry*, vol. 37, No. 10, (1994), pp. 385-401.
Gu et al. Photo-fries reactions of 1-Naphthyl esters in cation-exchanged zeolite Y and Polyethylene media. *Journal of American Chemical Society*, vol. 121, (1999), p. 9467.
Harkin, D.P. Uncovering functionally relevant signaling pathways using microarray-based expression profiling. *Oncologist*, vol. 5, (2000), pp. 501-507.
Hasted, J.B. "Aqueous dielectrics." (1973) Chapman & Hall, London. pp. 1- 255.
Hergenrother et al. Small-molecule microarrays: covalent attachment and screening of alcohol-containing small molecules on glass slides. *Journal of American Chemical Society*, vol. 122, (2000), pp. 7849-7850.
Hilpert et al. Anti-c-myc antibody 9E10: epitope key positions and variability characterized using peptide spot synthesis on cellulose. *Protein Engineering*, vol. 14, (2001), pp. 803-806.
Holzworth et al. Enhanced microwave heating of nonpolar solvents by dispersed magnetic nanoparticles. *Industrial and Engineering Chemistry Research*, vol. 37, (1998), p. 2701.
Huhmer et al. Noncontact infrared-mediated thermocycling for effective polymerase chain reaction amplification of DNA in Nanoliter volumes. *Analytical Chemistry*, vol. 72, (2000), pp. 5507-5512.
Jacobs et al. Combinatorial chemistry—applications of light-directed chemical synthesis. *Trends in Biotechnology*, vol. 12, (1994), pp. 19-26.
Jansen et al. "Advanced zeolite science and applications" in Jansen et al., eds., Elsevier, New York. 1994. pp. 215-250.
Jiang et al. Template-directed preparation of macroporous polymers with oriented and crystalline arrays of voids *Journal of American Chemical Society*, vol. 121, (1999), p. 11630.
Jin et al. Application of microwave techniques in analytical chemistry. *Trends in Analytical chemistry*, vol. 18, (1999), pp. 479-484.
Johnson, B. All's well that ends well: a profile of specialty microwell plates. *The Scientist*, vol. 13, (1999), p. 16.

Jones, K.D. Membrane immobilization of nucleic acids: Part !: Substrates. *IVD Technology*, vol. 7, No. 6, pp. 50-54, (Jul. 1, 2001).

Kappe, C.O. High-speed combinatorial synthesis utilizing microwave irradiation. *Current Opinion in Chemical Biology*, vol. 6, (2002), pp. 314-320.

Kappe, C.O. Speeding up solid-phase chemistry by microwave irradiation: a tool for high-throughput synthesis. *American Laboratory*, vol. 23, (2001), pp. 13-19.

Kempe et al. An approach towards surface imprinting using the enzyme ribonuclease A *Journal of Molecular Recognition*, vol. 8, (1995), p. 35.

Kidwai et al. A novel enzymatic synthesis of 2-substituted Naphtho[2,1-b]-pyran-3-ones using microwaves. *Indian Journal of Chemistry Section B: Organic Chemistry including Medicinal Chemistry*, vol. 37B, (1998), p. 963.

Korbel et al. Reaction microarrays: a method for rapidly determining the enantiomeric excess of thousands of samples. *Journal of American Chemical Society*, vol. 123, (2001), pp. 361-362.

Kramer et al. Synthesis and screening of peptide libraries on continuous cellulose membrane supports. *Methods in Molecular Biology*, vol. 87, (1998), pp. 25-39.

Kricka, L.J. Nucleic acid detection technologies—labels strategies, and formats. *Clinical Chemistry*, vol. 45, (1999), pp. 453-458.

Krishnan et al. Solid-phase extraction techniques for the analysis of biological samples. *Journal of Pharmaceutical and Biomedical Analysis*, vol. 12, (1994), pp. 287-294.

Kubrakova, I.V. Effect of microwave radiation on physiochemical process in solutions and heterogeneous systems: applications in analytical chemistry. *Journal of Analytical Chemistry*, vol. 55, (2000), pp. 1113-1122.

Laszlo, T.S. Industrial applications of microwaves. *The Physics Teacher*, (Nov. 1980), pp. 570-579.

Leitzel et al. Detection of cancer cells in peripheral blood of breast cancer patients using reverse transcrioption-polymerase chain reaction for epidermal growth factor receptor. *Clinical Cancer Research*, vol. 4, (1998), pp. 3037-3043.

Lennon, G.G. High-throughput gene expression analysis for drug discovery. *Drug Discovery Today*, vol. 5, (2000), pp. 59-66.

Leonhardt et al. Enzyme-mimicking polymers exhibiting specific substrate binding and catalytic functions. *Reactive Polymers*, vol. 6, (1987), p. 285.

Lew et al. Increasing rates of reaction: microwave-assisted organic synthesis for combinatorial chemistry. *Journal of Combinatorial Chemistry*, vol. 4, (2002), pp. 95-105.

Lidstrom et al. Enhancement of combinatorial chemistry by microwave-assisted organic synthesis. *Combinatorial Chemistry and High Throughput Screening*, vol. 5, (2002), pp. 441-458.

Lidstrom et al. Microwave-assisted organic synthesis—a review. *Tetrahedron*, vol. 57, (2001), pp. 9225-9283.

MacBeath et al. Printing small molecules as microarrays and detecting protein—ligand interactions en Masse. *Journal of American Chemical Society*, vol. 121, (1999), pp. 7967-7968.

Makote et al. Dopamine recognition in tepmlated silicate films. *Chemical Communications*, vol. 3, (1998), p. 425.

Marx, J. DNA arrays reveal cancer in its many forms. *Science*, vol. 289, (2000), pp. 1670-1672.

Mathew-Krotz et al. Imprinted polymer membranes for the selective transport of targeted neutral molecules. *Journal of American Chemical Society*, vol. 118, (1995), p. 8134.

Maugh, T. H. Semisynthetic enzymes are new catalysts. *Science*, vol. 222, (1984), pp. 151-153.

Maugh, T.H. Catalysts that break nature's monopoly. *Science*, vol. 221, (1983), pp. 351-354.

Maugh, T.H. Need a catalyst? Design an enzyme. *Science*, vol. 223, (1983), pp. 269-271.

Mingos et al. Applications of microwave dielectric heating effects to synthetic problems in chemistry. *Chemical Society Reviews*, vol. 20, (1991), pp. 1-47.

Mokaya, R. Ultrastable mesoporous aluminosilicates by grafting routes. *Angewandte Chemie International Edition*, vol. 38, (1999), p. 2930.

Narrlow et al. Acrylic polymer preparations containing recognitions sites obtained by imprinting with substrates. *Journal of Chromatography*, vol. 229, (1984), p. 29.

Nesatyy et al. Microwave-assisted protein staining: mass spectrometry compatible methods for rapid protein visualization. *Rapid Communications in Mass Spectrometry*, vol. 16, (2002), pp. 272-280.

O'Shannessy et al. Molecular imprinting of aminoacid derivatives at low temperature (0°C) using photolytic homolysis of azobisnitriles. *Analytical Biochemistry*, vol. 177, (1989), p. 144.

O'Shannessy et al. Recent advances in the preparation and use of molecularly imprinted polymers for enantiomeric resolution of amino acid derivatives. *Journal of Chromatography*, vol. 470, (1989), p. 391.

Olmedo et al. Microwave absorbing materials based on conducting polymers. *Advanced Materials*, vol. 5, (1993), p. 373.

Pasinetti, G.M. Use of cDNA microarray in the search for molecular markers in the onset of Alzheimer's disease dementia. *Journal of Neuroscience Research*, vol. 65, (2001), pp. 471-476.

Robinson, J.K. New molecular beacon technology. *American Laboratory*, (Dec. 2000), pp. 28-34.

Roda et al. Bio- and Chemiluminescence in Bioanalysis. *Fresenius Journal of Analytical Chemistry*, vol. 3(2000), pp. 752-759.

Rouhi, A.M. Boxed in: chemistry in confined spaces. *Chemical and Engineering News*, (Aug. 27, 2001), pp. 40-47.

Roussy et al. "Foundations and industrial applications of microwave and radio frequency fields." (1995) John Wiley & Sons, NY. pp. 445-466.

Schena et al. Quantitative monitoring of gene expression patterns with a complementary DNA microarray. *Science*, vol. 270, (1995), pp. 467-470.

Schmalzing et al. Capillary electrophoresis-based immunoassays. *Electrophoresis*, vol. 21, (2000), pp. 3919-3930.

Seiden et al. "PCR- and RE-PCR-based methods of tumor detection: potential applications and clinical implications." (1996) Important advances Oncol. Lippincott-Raven, Philadelphia, PA. pp. 191-204.

Shi et al. Template-imprinted nanostructured surfaces for protein recognition. *Nature*, vol. 398, (1999), pp. 593-597.

Sidransky, D. Nucleid acid-based methods for the detection of cancer. *Science*, vol. 278, (1997), pp. 1054-1058.

Slyadnev et al. Photothermal temperature control of a chemical reaction on a microchip using an infrared diode laser. *Analytical Chemistry*, vol. 73, (2001), pp. 4037-4044.

Stein et al. "Microwave processing of materials", Committee on microwave Processing of Materials, National Materilas Advisory Board, Commission on Engineering and Technical Systems, and National Research Counsil (1994) Microwave processing of Materials. Washington, DC, National Academy Press.

Varma, R. Microwave accelerated solvent-free chemical reactions. AMPERE Newsletter, Issue 29, ISSN 1361-8598, pp. 3-4, (2001).

Wathey et al. The impact of microwave-assisted organic chemistry on drug discovery. *Drug Discovery Today*, vol. 7, (2002), pp. 373-380.

Wood, W.G. Luminescence immunoassays: problems and possibilities. *Journal of Clinical Chemistry and Clinical Biochemistry*, vol. 22, (1984), pp. 905-918.

Yang et al. Heirarchically ordered oxides. *Science*, vol. 282, (1998), p. 2244.

Yu et al. Enhanced coupling efficiency in solid-phase peptide synthesis by microwave irradiation. *Journal of Organic Chemistry*, vol. 57, (1992), pp. 4781-4784.

Zlotorzynski, A. The application of microwave radiation to analytical and enbironmental chemistry. *Critical Reviews in Analytical Chemistry*, vol. 25, (1995), p. 43.

Zubritsky, E. Spotting a microarray system. *Modern Drug Discovery*, (May 2001), pp. 59-71.

Supplementary European Search Report corresponding to the European Patent Application No. 01979344.7-2404 / 1535071 dated Aug. 3, 2010.

Alexandratos and Natesan, "Coordination Chemistry of Phosphorylated Calixarenes and Their Application to Separations Science," Ind. Eng. Chem. Res., vol. 39, pp. 3998-4010 (Sep. 14, 2000).

Anzai et al., "Enzyme sensors prepared by layer-by-layer deposition of enzymes on a platinum electrode through avidin-biotin interaction," Sensors and Actuators, vol. 52, No. 1-2, pp. 3-9 (Sep. 15, 1998).

Badzian et al., "Nucleation and growth phenomena in chemically vapor-deposited diamond coatings," Surface and Coatings Technology, vol. 36, No. 1-2, pp. 283-293 (Dec. 1, 1988).

Halling et al., "Hydrolysis of Lactose in Milk by Lactase Immobilized to a Non-Porous Magnet Support," European Journal of Applied Microbiology and Biotechnology, vol. 8, No. 1-2, pp. 27-36 (1979).

Harada, A., "Construction of Supramolecular Structures from Cyclodextrins and Polymers," Carbohydrate Polymers, vol. 34, No. 3, pp. 183-188 (Dec. 20, 1997).

Kawakami et al., "Immobilization of Glucose Oxidase of Polymer Membranes Treated by Low-Temperature Plasma," Biotechnology and Bioengineering, vol. 32, No. 3, pp. 369-373 (1988).

Laurell et al., "Enhanced Enzyme Activity in Silicon Integrated Enzyme Reactors Utilizing Porous Silicon as the Coupling Matrix," Sensors and Actuators B, vol. 31, No. 3, pp. 161-165 (Mar. 1, 1996).

Mehvar, R., "Modulations of the Pharmacokinetics and Pharmacodynamics of Proteins by Polyethylene Glycol Conjunctions," Journal of Pharmacy and Pharmaceutical Sciences, vol. 3, No. 1, pp. 125-136 (Jan. 1, 2000).

Official Action corresponding to U.S. Appl. No. 10/842,512 dated Oct. 5, 2011.

Office Communication corresponding to the European Patent Application No. 03 794 447.7-2404 dated Dec. 17, 2010.

Office Communication corresponding to the European Patent Application No. 01979344.7-2404 dated Dec. 29, 2010.

Hailing et al., "Hydrolysis of Lactose in Milk by Lactase Immobilized to a Non-Porous Magnet Support," European Journal of Applied Microbiology and Biotechnology, vol. 8, No. 1-2, pp. 27-36 (1979).

Alves da Silva et al., "Photopolymerization of acrylamide onto magnetite particles: preparation of magnetic supports for enzyme immobilization," Materials Letters, vol. 11, pp. 96-100 (1991).

Antia & Govind, "Applications of binderless zeolite-coated monolithic reactors," Applied Catalysis A: General, vol. 131, pp. 107-120 (1995).

Cantarella et al., "Cellulose Hydrolysis and Fermentation," Proceedings of a CEC Workshop, pp. 186-195 (1992).

Cho and Bailey, "Immobilization of Enzymes on Activated Carbon: Properties of Immobilized Glucoamylase, Glucose Oxidase, and Gluconolactonase," Biotechnology and Bioenginerring, vol. 20, pp. 1651-1665 (1978).

Communication Pursuant to Article 94(3) EPC corresponding to European Patent Application No. 01 979 344.7-2404 dated Jan. 29, 2010.

Noguchi et al., "Comparison of Enzyme Immunoassay with Dextran-coated Charcoal Method in the Determination of Progesterone Receptor in Breast Cancer Cytosols," Eur. J. Cancer Clin. Oncol., vol. 24, pp. 1715-1719 (1988).

Suwa et al., "Magnetic Resonance Imaging of Esophageal Squamous Cell Carcinoma Using Magnetite Particles Coated with Anti-Epidermal Growth Factor Receptor Antibody," Int. J. Cancer, vol. 75, pp. 626-634 (1998).

Tarasevich, "293-Electrocatalysis of a Gathodie Oxygen Reduction by Laccase," Bioelectrochemistry and Bioenergetics, vol. 6, pp. 393-403 (1979).

Valtchev & Mintova, Zeolites, "The effect of the metal substrate composition on the crystallization of zeolite coatings," vol. 15, pp. 171-175 (1995).

Yamamoto et al., "Immobilization of a bio-catalyst (enzyme) on a ceramic surface treated by the SPCP-CVD method," Advanced Powder Technol., vol. 7, pp. 271-277 (1996).

* cited by examiner 1. microwave irradiation

2. Composite consisting of;
   (a) material that is highly susceptible to microwave heating, and
   (b) material that physically transforms upon heating.

3. A fluid close enough to the heat-transformable material (b) to be physically affected by physical changes in said material.

Heat shrink tubing coated in middle with dielectric paint 600W microwaves/30 seconds Heat shrink tubing on dielectric (shaded) half-undercoated glass slide 600W microwaves/30 seconds Top View:
1. Nitrocellulose covered glass microscope slide
2. Heat shrink tubing, plugged on one end (left), filled with oxidant solution
3. Spotted chemiluminescent reagent Bottom View:
4. MCS/SS6M dielectric layer (0.04" thick)
5. BCR-1/SS6M dielectric layer (0.01" thick)

1. Half of slide undercoated with BSR-1/SS6M dielectric.

2. Top of slide coated with thin layer of paraffin wax.

3. Two spots of KmnO₄ (10 μL each) pipetted.

4. Wax "dome" added over KmnO₄ droplets.

5. Upon mild microwaving, KmnO₄ droplet released only on dielectric side.

i          ii

1.

2.

3.

4.

MICROWAVE MICROFLUIDICS

CROSS-REFERENCE TO RELATED APPLICATIONS

This application is a continuation-in-part of U.S. patent application Ser. No. 10/234,092 (filed on Sep. 5, 2002), which is a continuation-in-part of U.S. patent application Ser. No. 09/968,517 (filed on Oct. 2, 2001), both of which applications are herein incorporated by reference in their entireties. This application also claims priority from U.S. Patent Application Ser. No. 60/237,192 (filed Oct. 3, 2000), which applications is herein incorporated by reference in its entirety.

FIELD OF THE INVENTION

The present invention relates to the field of microwave heating. It also relates to "smart" materials, which physically respond to environmental stimuli to perform tasks. It also relates to the field of microfluidics, especially in the field of biomedical analyses on microchips.

BACKGROUND OF THE INVENTION

Until now, no one has controlled the motion of fluids as disclosed herein. Devices are used that emit radiofrequency/microwave energy. The energy is directed to a target object, for example, a microchip that contains one or more material(s) that absorb(s) microwave energy. The microwave-generated heat energy causes physical changes in fluid-containing compartments, which in turn causes fluid movement.

Microfluidics

Microfluidics deals with the movement of small amounts of fluid (Burtsoff, 2004; Fitzgerald, 2002; Lesney, 2002; Roper et al., 2003; Hansen & Quake, 2003; Beebe et al., 2002; McDonald et al, 2000). Microfluidics is key toward the development of micro-synthesis, micro-separations, and lab-on-a-chip (or BioMEMS, biological MicroElectroMechanical Systems) technologies. Microfluidics assists in sample-preparation, rinsing, mixing, reaction, and other fluid handling needs for small volumes that cannot be performed in traditional ways. It is expected that microfluidics will revolutionize many applications including; proteomics and genomics research, high throughput and small sample analysis, on-site field and environmental analysis, clinical diagnostics, small-quantity chemical reactions, and combinatorial chemistry synthesis (McDonald et al., 2000). Additional benefits of microfluidics include automation, reduced waste, improved precision and accuracy, and disposability.

Microfluidics is a multi-faceted technology. Sub-technologies include electrophoresis, electrodynamics, semiconductor fabrication methods, fluid-moving technologies, labeling technology, laser fluorescence, and inkjet printing. This invention is concerned with the movement and mixing of fluids on a microfluidics platform, such as a chip.

Numerous approaches to moving fluids on microfluidics devices have been proposed and developed. These include; centrifugal force (Burtsoff, 2004), electrophoresis (Roper et al., 2003), electrokinetic pumping (Becker & Gartner, 2000), microsolenoid-triggered syringe pumps, piezoelectric pumps, gas bubble production (Lesney, 2002), hydrodynamic focusing, and passive fluid control (hydrophilic/hydrophobic repulsion) (Fitzgerald, 2002). Prior to this disclosure, microwave energy has not been used to move fluids.

Smart Materials

So-called smart materials are materials that can sense and dramatically respond to an environmental stimulus. Physical changes in smart materials include, but are not limited to; growth or shrinkage, precipitation, solubilization, and color change. Some examples are shown in Table 1 (Roy & Gupta, 2003, Morrison & Mosier, 2000, Fong, et al. 2002; Jeong & Gutowska, 2002).

TABLE 1

Examples of Smart Materials

| Stimulus | Responsive Materials |
|---|---|
| pH | Dendrimers, poly(L-lysine) ester, poly(hydroxyproline), polysilamine, Eudragit S-100, chitosan, PMAA-PEG copolymer |
| $Ca^{2+}$ | alginate |
| $Mg^{2+}$ | chitosan |
| organic solvent | Eudragit S-100 |
| temperature | PNIPAAm, poloaxymers, chitosan-glycerol phosphate-water, prolastin, polymer/protein hybrid hydrogels |
| magnetic field | PNIPAAm hydrogels containing ferromagnetic material |
| redox reaction | PNIPAAm hydrogels containing tris (2,2'-bipyridyl) ruthenium II |
| electric potential | polythiophen gel |
| IR radiation | Poly(N-vinyl carbazole) composite |
| UV radiation | Polyacrylamide crosslinked with 4-(methacryloylamino) azobenzene |
| ultrasound | Dodecyl isocyanate-modified PEG-grafted poly(HEMA) |
| microwave radiation | organic/aqueous liquid phase mixing |

Smart materials can be used in bioseparation (Fong et al., 2002; Hoffman, 2000), drug delivery (Morrison & Mosier, 2000), tissue engineering, and gene delivery in gene therapy. They can also be used as molecular gates and switches, to aid in protein folding, and in flow control in microfluidics (Roy & Gupta, 2003).

Microwave Heating

Microwaves (including radiofrequency or RF electromagnetic radiation) are commonly used in wireless communication devices. Advances in microwave transmission have improved along with tremendous recent technological improvements in the satellite and communications industry (for example, in cell phones and wireless internet).

Microwaves are also well known in common kitchen appliances. Microwave ovens heat water-containing food rapidly because water is efficient at converting microwave energy to thermal energy. Kitchen microwave ovens emit microwaves at a frequency of 2.45 GHz, which is within the microwave absorption spectrum of water. Frequencies outside of the absorption spectrum of water would not heat food as well.

Another use for microwave heating is in chemical reaction applications (Bose et al., 1997; Bradley, 2001; Wathey et al., 2002; Lew et al., 2002). Microwave chemistry refers to the use of microwaves to accelerate chemical reactions (Mingos & Baghurst, 1991; Zlotorzynski, 1995). Microwave ovens specifically designed for use in carrying out microwave chemistry of bulk reaction solutions are commercially available (CEM Corporation (Matthews, N.C.), Milestone, Inc. (Monroe, Conn.), Biotage AB (Uppsala, Sweden), and PerkinElmer Instruments (Shelton, Conn.).

In yet other cases, microwave heating has been used in biochemistry applications. Microwave heating has been used to assist in protein staining (Nesatyy et al., 2002; Jain, 2002). Bulk microwave heating of samples has been used to accelerate antibody-antigen binding reactions in immunoassays, immunohistochemical assays, and DNA in-situ hybridization assays (Leong & Milios, 1986; Hjerpek et al., 1988; van den Kant et al., 1988; Boon & Kok, 1989; Kok & Boon, 1990; van den Brink et al., 1990; Slap 2003). In another case, microwaves were used as a heat source during PCR (Fermer et al., 2003).

The present invention is unique in that it discloses a novel means of using microwave energy to move and mix liquids without necessarily heating the liquids that are to be moved (isothermal fluid movement). Microwaves cause physical changes in materials that transform to induce fluidic effects.

Directed Microwave Heating

Dielectric materials are good at absorbing microwaves. Dielectrics have unique spectral characteristics of frequency versus heating ability, with different substances heating more effectively at different frequencies (Gabriel et al., 1998). Although dielectric heating is referred to here as microwave heating, dielectric heating can also occur at radio frequencies. This invention is intended to include those effects.

Dielectric heating depends on a number of factors including the frequency of the microwave irradiation and the absorption properties of the dielectric at that frequency. All dielectric materials have characteristic absorption spectra (frequency vs. heating ability). For example, in a conventional kitchen microwave oven, the microwave frequency (2.45 GHz) is very good for heating water, but not good for heating other materials (for example, a cup that holds the water). If the frequency of the microwave emission would be changed, in theory one could heat the cup but not the water (depending on the relative dielectric absorption characteristics of water and the cup).

In this invention, microwaves heat materials that are especially good at absorbing microwaves. The microwave-active materials are in thermal proximity to heat-susceptible materials. When the microwave-susceptible material is irradiated with microwaves, the heat susceptible material physically changes, causing fluid movement. The heat-susceptible materials need not be, by themselves, microwave-susceptible. Preferably, they will not be significantly microwave-susceptible. Most preferably, they will not be microwave-susceptible.

The invention has several advantages over alternative heating methods. These alternative methods include IR heating (for example, using a lamp, hair drier, or heat gun) and resistive heating. Resistive heating requires direct contact of the reaction surface with an electrical circuit and resistor, while the present invention obviates the need for direct contact. IR heating, although non-contact, is less efficient in rapidly heating a surface than is microwave heating. Finally, it is difficult to target infrared radiation, such as from a heat gun, especially in a millimeter or centimeter resolution pattern.

OBJECTS OF THE INVENTION

The invention is directed toward an improved process and apparatus for moving volumes of fluid on demand, especially sub-millimeter volumes. Another objective of the invention is to release fluids from a storage compartment (microwave-opened valve). It is another objective of the invention is to move fluids without the requirement for pumps or motors. Another objective of the invention is to move fluids using an electromagnetic irradiation power source. Another objective of the invention is to render materials that are heat responsive, but not microwave responsive, susceptible to microwave heating. It is another objective to cause materials that have smaller dimensions than the wavelength of a microwave to be susceptible to microwave heating. It is another objective of the invention that fluid movement be highly controllable, so that a user at can selectively initiate it at will. It is another objective of the invention that the fluidics may take place on a single-use disposable cartridge. It is yet another objective of the invention to deliver liquids using microwave irradiation without heating the moved fluid.

SUMMARY OF THE INVENTION

Figure 1:
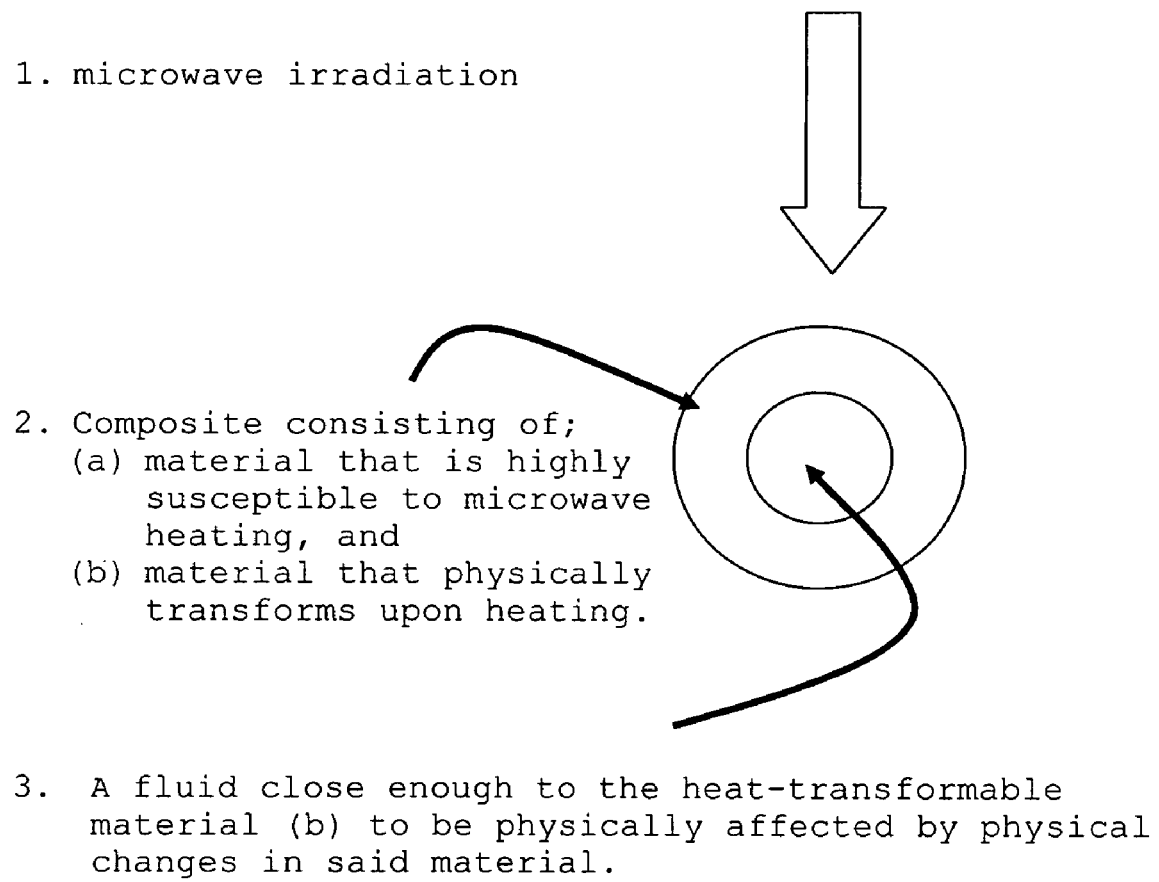
FIG. 1: The four components of a preferred embodiment of the microwave microfluidics of the present invention: (1) microwave irradiation, a composite of (2) microwave sensitive material and (3) heat-transformable material, and (4) fluid.

The invention describes methods and compositions of matter whereby targeted microwave radiation causes liquids to move and/or mix. In the invention, microwave irradiation causes temperature increases in materials that are highly susceptible to microwave heating ("lossy" materials). The lossy materials are in thermal proximity to materials that physically change in response to heat. The physical changes, which include melting and shrinking, cause compartmentalized fluids to move. Hence, the four components of a preferred embodiment of the invention are: (1) microwave irradiation, (2) the microwave susceptible material, (3) a heat-sensitive material, and (4) a fluid (FIG. 1). Fluid movement may ultimately result in a chemical reaction. The specific chemical reaction can be used for preparative, analytical, and/or decontamination applications. In analytical applications, the reaction may optionally be monitored and/or quantitated, for example in medical diagnostics, by an accompanied observable physico-chemical change (color change, for example). In preparative applications, the presence of a microwave-dielectric layer can assist in surface chemistry to prepare the solid support for subsequent analytical reactions or be used to accelerate heat-dependent molecular binding and amplification reactions. In decontamination applications, fluidics can be used to deliver reagents such as bleach or acid, which serve to render toxic or pathogenic samples inert following an analysis.

In detail, the invention provides A method for moving a fluid comprising;
(a) applying electromagnetic radiation to a composite comprised of at least a first, microwave-absorbing, material that increases in temperature upon absorption of the electromagnetic radiation, and a second material that is in thermal proximity to the first material, in contact with the fluid, and which is capable of melting or changing shape upon heating; and
(b) allowing the microwave-absorbing material to undergo a temperature change sufficient to cause the second material to substantially melt or change shape, causing movement of the fluid.

The invention further concerns the embodiment of such method wherein the wavelength of the applied electromagnetic radiation is between 5 cm and 100 m.

The invention further concerns the embodiments of such methods the first material contains one or more material(s) selected from the group consisting of carbon, clay, $BaTiO_3$, inorganic titanates, inorganic niobates, ferroelectric polymers, $Al_2O_3$—$Fe_3O_4$, $Fe_3O_4$, organic polymers, aluminum-epoxy composites, silicon oxides, $LaCoO_3$, $LaSrO_3$, $LaMnO_3$, $LaFeO_3$, SiC, AlN, ZnO, MgO—SiC, $Al_2O_3$, AlN—SiC, CrB, $Fe_2B$, $SiC/SiO_2$, alumina, mullite, zircon, MgO, $Si_3N_4$, Si, Mg, FeSi, $Cr_2O_3$, MgO, $MnO_2$, NiO, calcium aluminate, ITO, Nb, TaC, SiC, $MoSi_2$, Cu, Fe, $ZrO_2$, $Y_2O_3$, zirconium oxynitrate, aluminum nitrate, yttrium nitrate, and ferrites.

The invention further concerns the embodiments of such methods wherein the second material contains one or more material(s) selected from the group consisting of polyolefin, fluoropolymer, chlorinated polyolefin, highly flexible elastomer, wax, lipid, and phospholipid.

The invention further concerns the embodiments of such methods wherein the fluid is an aqueous or organic liquid, wherein the temperature change is between 1° C. and 200° C., wherein the direction of the fluid movement is linear, branched, expanding planar, or expanding spherical, wherein the fluid movement initiates a chemical reaction involving one or more solutes of the fluid and/or wherein the fluid movement initiates a chemical reaction involving one or more solutes in the fluid, and in which the extent or rate of the chemical reaction can be measured.

The invention also concerns a composite and fluid system comprising a fluid, a solid material that absorbs microwave radiation resulting in dielectric heating and a solid material that substantially melts or changes shape in response to an increase in temperature, whereby application of electromagnetic radiation to the composite-fluid system results in movement of the fluid.

The invention further concerns the embodiment of such a composite and fluid system wherein the dielectric heating responsive solid material contains one or more material(s) selected from the group consisting of carbon, clay, $BaTiO_3$, inorganic titanates, inorganic niobates, ferroelectric polymers, $Al_2O_3$—$Fe_3O_4$, $Fe_3O_4$, organic polymers, aluminum-epoxy composites, silicon oxides, $LaCoO_3$, $LaSrO_3$, $LaMnO_3$, $LaFeO_3$, SiC, AlN, ZnO, MgO—SiC, $Al_2O_3$, AlN—SiC, CrB, $Fe_2B$, $SiC/SiO_2$, alumina, mullite, zircon, MgO, $Si_3N_4$, Si, Mg, FeSi, $Cr_2O_3$, MgO, $MnO_2$, NiO, calcium aluminate, ITO, Nb, TaC, SiC, $MoSi_2$, Cu, Fe, $ZrO_2$, $Y_2O_3$, zirconium oxynitrate, aluminum nitrate, yttrium nitrate, and ferrites.

The invention further concerns the embodiments of such composite and fluid systems wherein the microwave radiation is radiofrequency radiation, wherein the dielectric heating responsive material is capable of dielectric heating to a sufficient degree to substantially cause melting or a shape change in the temperature responsive material and movement of the fluid, wherein the temperature responsive material contains one or more material(s) selected from the group consisting of polyolefin, fluoropolymer, chlorinated polyolefin, highly flexible elastomer, wax, lipid, and phospholipids, and/or wherein the fluid is an aqueous or organic liquid.

The invention also concerns an instrument for moving a fluid, wherein the instrument comprises:
(a) a source of emitted electromagnetic radiation;
(b) a composite and fluid system, wherein the composite comprises at least a first, microwave-absorbing material, and a second material that is in thermal proximity to the first material and which is capable of melting or changing shape upon heating, wherein the temperature of the microwave-absorbing material increases as a result of the application of the electromagnetic radiation, and wherein the temperature increase causes the second material to substantially melt or change shape, and results in the movement of the fluid.

The invention further concerns the embodiment of such an instrument wherein the fluid movement is linear, branched, expanding planar, or expanding spherical, and/or wherein the wavelength of the electromagnetic radiation is between 5 cm and 100 m.

DEFINITIONS

Aqueous Solution: A liquid medium that is more than 50% water by volume.

Capillary action (force): A force that moves fluids when the adhesion to the walls is stronger than the cohesive forces between the liquid molecules.

Capsule: A reservoir used to contain liquids on a cartridge prior to use. Examples of capsules include channels, networks of channels, vesicles, and laminar lipid layers.

Cartridge: A vessel or device in which a reaction takes place. The cartridge may be coated with a dielectric. Well-known examples of cartridges are microarray chips and labs-on-a-chip.

Channel: A nonporous open groove or enclosed tube with a length-to-diameter aspect ratio of greater than 2.0.

Chip: An essentially planar object that has one or more zones on its surface for desired chemical reactions to take place. A chip is preferably small enough and light enough to be held in one hand. If biological molecules are involved in the reactions, the chip is also known as a biochip.

Compartment: A reservoir that is 50% or more enclosed by a nonporous material.

Composite: Two or more distinct types of solid, liquid, or gaseous materials. The physical properties of at least one of the materials can be affected by the physical properties of at least one of the other materials. The materials may be blended or physically distinct.

Dielectric Heating: Heating of a dielectric (electrically-insulating) material by electromagnetic radiation in the wavelengths between approximately 5 cm and 100 m.

Fluid: A liquid or a gas.

Lab-On-A-Chip: A planar device where liquids are moved around either to mix them together for chemical reactions or to deliver them to analysis functionalities to generate information.

Lossy Material: A (dielectric) material that loses absorbed microwave energy in the form of heat.

Lossy Medium: A medium in which a significant amount of the energy of a propagating electromagnetic wave is absorbed per unit distance traveled by the wave.

Macroarray: A panel of a plurality of reaction zones on a chip ranging from 1 to 1000 zones.

Microarray: A panel of reaction zones on a chip numbering greater than 1000.

Microwave: As used herein microwave is intended to denote both electromagnetic radiation in the range of $3\times10^2$ to $3\times10^4$ MHz (wavelengths of 1 m to 1 cm), as well as longer (radio) wavelengths (up to 100 m) at which dielectric heating occurs, which can be alternatively used. Overall, microwave heating (herein defined to include radiofrequency dielectric heating) frequencies span wavelengths of about 1 cm to 100 m.

Microwave Oven: A device that emits microwave radiation at a pre-determined wavelength into an internal chamber. The chamber is typically closed or partially closed in order to limit the escape of microwaves.

Microwave Susceptible Material: A substance that is lossy at microwave or radiofrequency wavelengths.

Organic Solution: A liquid medium that is more than 50% organic solvent by volume.

Smart Materials: Materials that can sense and dramatically respond to an environmental stimulus.

Thermal Proximity: The situation in which one substance of a higher temperature is close enough to a second substance of lower temperature that it will transfer heat from the first substance to the second substance.

Thermocouple: A sensor for measuring temperature consisting of two dissimilar metals, joined together at one end. The metals produce a small unique voltage at a given temperature. The voltage is measured and interpreted by a thermocouple thermometer.

Vesicle: A hollow spherical capsule.

Waveguide: A structure that causes a wave to propagate in a chosen direction. It is accomplished by an intimate connection between the waves and the currents and charges on the boundaries, or by some condition of reflection at the boundary.

Wicking action (force): The movement of water by forces of attraction (both capillary and chemical) between the water and the adsorbing material.

DETAILED DESCRIPTION OF THE PREFERRED EMBODIMENTS

Physical Components of a Preferred Embodiment of the Invention:

The physical components of a preferred embodiment of the invention are:

1) The Microwave Generating Instrument. The instrument contains; (a) a microwave source and (b) one or more reaction chamber(s). The instrument also optionally contains; (c) a means of controlling the temperature in real time and (d) one or more detection system(s) to measure physiochemical changes in the sample (e.g., light emission and temperature). Each of these will be considered separately here.

a) Microwave source. Microwaves can be generated by various devices including, for example, a magnetron, a solid-state device (such as a Bluetooth or Wi-Fi device (e.g., an IEEE 811.b device)), a klystron, a cross-field amplifier, a traveling wave tube, a backward-wave oscillator, or any combination thereof. The microwave emission is in the frequency range of 300 to 30,000 MHz (wavelengths of 1 m to 1 cm). Dielectric heating also occurs at lower (radio) frequencies of down to 3 MHz (wavelengths of up to 100 m), which can be alternatively used in accordance with the principles of the present invention. Overall, microwave/dielectric heating frequencies span wavelengths of about 1 cm to 100 m. Electromagnetic heating throughout this range is considered part of this invention. The ideal frequency used depends on factors including the identity of the dielectric material to be heated. As described above, there are many devices that generate microwaves—most notable for the present invention are magnetrons and solid-state devices. Low power magnetrons (500-1200 W) commonly found in kitchen microwave ovens are sufficient for the invention. Alternatively, solid-state devices, such as Bluetooth or Wi-Fi chips, which are commonly used in wireless communication devices may be employed. Such devices emit low power (<1 W) microwaves at the same frequency as kitchen microwave ovens (2.45 GHz). These devices, which are roughly the size of a house key, are much smaller than light-bulb-sized magnetrons. Hence, solid-state devices can generate microwave power in a handheld device. The low power levels are sufficient for use in this invention, especially if the dielectric heats well and if the sample to be heated is placed in a waveguide (see below).

Attractive frequencies for this invention include 0.915 GHz, 2.45 GHz, 5.85 GHz, and 22.125 GHz. The U.S. Government currently approves these frequencies for use for industrial, scientific, and medical uses (Boon & Kok, 1989). Other frequencies may also be attractive provided that the emission within the microwave chamber is sufficiently shielded (to prevent interference with communications uses of microwaves). Of the above-listed frequencies, 2.45 GHz is attractive because it is a widely accepted frequency used in numerous existing devices such as domestic microwave ovens and many wireless communications devices (Wi-Fi and Bluetooth). Because of widespread use of these devices, design and manufacturing know-how of 2.45 GHz emitters including magnetrons and solid-state devices are well known. A frequency of 0.915 GHz is also an attractive frequency for aqueous applications because water is least susceptible to dielectric heating at this frequency (Laslo, 1980).

b. Reaction chamber. The reactions may be carried out within an open cavity, such as a microwave oven or a waveguide. Both microwave ovens and waveguides are well known in the art and readily adaptable to directed microwave chemistry.

In the case of an oven cavity, it is preferable for the microwaves to be "homogenized" to prevent uneven heating/reactivity. This can be accomplished through the use of a rotating sample carousel or through the use of irregularities or deflectors in the oven, which would mix the microwaves.

A preferable chamber would be a waveguide (for example, sold by Coleman Microwave Company (Edinburg, Va.) and Gerling Applied Engineering, Inc. (Modesto, Calif.). Microwaves within a waveguide are very uniform. Moreover, the interior of a waveguide is small which can be readily used with correspondingly small chips and plates. One or more holes can be introduced into the waveguide for practical purposes, such as a slot for plate or chip insertion and an orifice for light or temperature measurement. Waveguides are widely available commercially and can also be custom designed based on known microwave algorithms.

The dielectric, which is targeted by microwaves, may either be permanently incorporated into the wall of the reaction chamber or be a part of the disposable device (e.g., a microarray chip). In the former case, the sample (a conventional chip) would be placed on the dielectric in the reactor chamber. In the latter case, the chip would be modified to include a dielectric.

An alternative reaction chamber to those described above is one that is outside of a microwave oven or waveguide, yet abuts a microwave chamber. When this type of reaction chamber is used, the sample would heat, but not come in direct contact with microwave irradiation. The sample would be placed in contact with a dielectric material that is physically built into the wall of the waveguide/oven cavity. The wall dielectric would heat from the interior microwave bath, and heat from the dielectric would thermally transfer to the outside surface where it would contact the sample. The advantage of this format is that microwaves would not directly contact the sample to be heated. Thus, materials incompatible with microwaves could be more easily used. For example, a metal thermocouple used to measure sample temperature might spark on the inside of a reaction chamber.

c. Temperature Controller. It is generally desirable to control the reaction temperature in real time. A thermocouple can be used to measure the temperature of the dielectric provided that the dielectric is structurally amenable (for example a chip-based dielectric. One example is if the dielectric is coated on a disposable chip (i.e., a microscope slide). A thermocouple could be used to contact the chip and monitor the temperature during heating. Moreover, thermocouple temperature measurement could be used to control the temperature by controlling the power of the microwave oven. If the dielectric temperature reached a certain level, say 95° C., the microwave could be automatically shut off. When the temperature dropped, to say 77° C., the thermocouple would cause the microwave to begin heating again. Such thermocouple-based temperature control is well known art (Huhmer & Landers, 2000; ASTM, 1993; Kreider, 1989). Alternatively, temperature can be measured using non-contact spectroscopic techniques (Boon & Kok, 1989; Slyanev et al., 2001). Both thermocouples and spectroscopic methods have been used to measure microchip temperatures (Huhmer & Landers, 2000; Slyanev et al. 2001).

d) Detection System(s). Detection is an attractive (but non-essential) component of this invention. Detection would be used in an analytical application of microfluidics, such as a medical diagnostics test. Detection may be carried out by a number of means such as fluorescence, absorbance, or chemiluminescence. We have shown that surface-directed microwave heating can preferentially enhance numerous chemical reactions, including reactions that are accompanied by measurable physicochemical changes, such as chemiluminescence. These observable reactions can be useful in microwave-based molecular analyses. For analytical applications, the reaction will be chosen depending on the preferred detection method (a change in color, luminescence, etc.). The detector is positioned opposing the reaction, for example a chip. It may be within the reaction chamber, but will preferably not interfere with reaction.

2) The Microwave-Absorbing Material. Numerous solid materials absorb microwaves and consequently heat rapidly. These materials are either pure or are composites with other materials, such as silicone or plastics. There are many materials that could function in this invention to absorb microwaves and heat such that the heat is transferred to affect a heat-transformable material.

One material with a high dielectric constant is barium titanate ($BaTiO_3$). The dielectric constant is 200-16,000 (compared with 80 for water). Barium titanate can be formed into films and has been used in analytical devices (Ewart et al.). Moreover, in addition to barium titanate, methods for forming thin and thick films of other ferroelectric materials at low temperature have improved steadily. Known high dielectric constant inorganic titanates, niobates, and ferroelectric polymers can be formed by many processes including low temperature chemical vapor deposition, laser photo-ablation deposition, sol-gel processes, RF magnetron sputtering, screen printing and firing, (in the case of the polymer) spin coating, and other methods (Yang et al., 1998).

Natural clay can also be used as a moldable dielectric. In addition, a 1:1 w/w mixture of alumina-magnetite ($Al_2O_3$—$Fe_3O_4$) can be used as a dielectric support that heats strongly (Bram et al., 1991). Magnetite ($Fe_3O_4$) particles heat well under microwave irradiation.

Another material that could be used is carbon. Forms of carbon include carbon black, activated charcoal, graphite, carbon nanotubes and nanospheres (such as $C_{60}$ and $C_{70}$).

Many additional dielectric materials can be identified by screening dielectrics for their ability to heat during microwave irradiation. Class I dielectrics (dielectric constants typically less than 150) and Class II dielectrics (dielectric constants typically in the range of 600-18,000) can be used (technical brochure, Novacap, Inc., Valencia Calif.). Other suitable materials include organic polymers, aluminum-epoxy composites, and silicon oxides. The microwave frequency can be varied as well. This simple screening procedure would yield conditions (frequency and material) that would direct heating toward the dielectric material.

Still other materials that heat substantially under RF irradiation include ferrites and ferroelectrics. In addition to $BaTiO_3$, described above, other Perovskites (minerals of the chemistry $ABX_3$) such as $NaNbO_3$, $LaCoO_3$, $LaSrO_3$, $LaMnO_3$, and $LaFeO_3$ heat well in a microwave field. Other materials that heat efficiently in a microwave and which could be used in the invention include SiC, AlN, ZnO, MgO—SiC, $Al_2O_3$, and AlN—SiC.

Other types of materials that are well known to heat dramatically under microwave irradiation are various ceramics; oxides ($Al_2O_3$, for example), non-oxides (CrB and $Fe_2B$, for example), and composites ($SiC/SiO_2$, for example). Numerous materials are processed (sintered, etc.) by exploiting their microwave heating characteristics.

Microwaves can heat composite materials. For example, materials that are normally transparent to microwaves can be heated by adding polar liquids or conducting particles. Refractory oxides such as alumina, mullite, zircon, MgO, or $Si_3N_4$ have been made to couple effectively with microwaves by the addition of electroconductive particles of SiC, Si, Mg, FeSi, and $Cr_2O_3$. Oxides including $Al_2O_3$, $SiO_2$, and MgO have been effectively heated by the addition of lossy materials such as $Fe_3O_4$, $MnO_2$, NiO, and calcium aluminate. Indium tin oxide (ITO) could also be used. Mixtures of conducting powders, such as Nb, TaC, SiC, $MoSi_2$, Cu, and Fe, and insulators such as $ZrO_2$, $Y_2O_3$, and $Al_2O_3$, have coupled well with microwaves. Various materials in solution (zirconium oxynitrate, aluminum nitrate, and yttrium nitrate) that are good couplers have also been added to enhance microwave absorption of powdered insulating oxides. A microwave absorbing heating mantle is sold by Milestone, Inc. made from a composite of graphitic carbon and Teflon. Microwave-absorbing materials are also sold by Emerson & Cuming Microwave Products, Inc. (Randolph, Mass.). These include ECCOSORB®, which are made from microwave-absorbing materials (carbon, iron, magnetically, or ferrite loaded) composited in a polymeric matrix such as silicone, vinyl or polyurethane. ECCOSORB® can be purchased in sheets of various sizes and thicknesses, with or without adhesive backing.

Addition of conductive materials in various shapes including powder, flake, sphere, needle, chip, or fiber, would cause the heating of low loss materials. For example carbon black or metal pieces with sizes ranging from 0.1-100 µm can increase the heating properties when used as inclusions. The nature and concentration of such materials can be optimized without undue experimentation.

The microwave-absorbing material can be an integral part of the microwave-generating instrument, or it can be an accessory thereof. In this case, the material would be situated in thermal proximity to the reaction surface. Alternatively, the microwave absorber can be incorporated into or applied to the bottom of a disposable reaction vessel such as a microarray chip of 96-well plate. Numerous application methods are available including painting (as an ink, such as carbon ink, or in a binder such as aqueous polyvinyl acetate (PVAc), screen printing (such as SiC in terpineol), or by adhesive attachment of a polymer composite (such as ECCOSORB®, Emerson & Cuming).

3) The Heat-Susceptible Material. In the broadest terms, the heat susceptible material can be any material that changes shape, combusts, evaporates, or melts upon heating. The preferred physical changes are melting of vesicle and contraction of heat-shrinkable plastics. Vesicles can be made from wax, lipids, or other material with a melting point below approximately 175° C. Heat shrinkable plastics, such as polyolefins are well known and often used in shrink-wraps and heat-shrinkable tubing. Typical applications of heat shrinkable tubing include: electrical insulation, abrasion protection, and weather sealing. Heat shrinkable tubing can be found in many major markets such as automotive, aerospace/aviation, military, spacecrafts, audio/video, telecommunications, shipbuilding, appliances, and rail/transit. Heat shrink tubing can be made from various plastics including polyolefin, fluoropolymer (PVC, FEP, PTFE, and Kynar PVDF), chlorinated polyolefin (Neoprene), and highly flexible elastomer (Viton).

Microfluidics channels and vesicles can be made off-cartridge and later added to the cartridge during manufacturing. For example, a channel could be glued to the surface of the cartridge. Alternatively, the microfluidics could be made on-cartridge. Numerous methods are known for incorporating microfluidics networks and reservoirs into cartridges or chips. There are many methods known in the art of forming vesicles and channels for microfluidics, including micromachining methods, hot embossing, wire imprinting, casting, extrusion, injection molding, optical and soft lithography, bonding, lamination, and gluing (Becker & Gartner, 2000; McDonald et al., 2000; Hansen & Quake, 2003; Chen & Chen, 2000; Beebe et al., 2002). These methods could also be used with many heat transformable materials such as waxes and polyolefins.

Hot embossing is essentially the stamping of a pattern into a polymer softened by raising the temperature of the polymer just above its glass transition temperature. The stamp used to define the pattern in the polymer may be made in a variety of ways including micromachining from silicon, LIGA, and machining using a CNC tool (for making large features). A wide variety of polymers have been successfully hot embossed with micron-scale (and below) size features, including polycarbonate and PMMA. This technique is used primarily for defining micro-channels and wells for fluidic devices. The benefits of this approach are the ability to take advantage of the wide range of properties of polymers, as well as the potential to economically mass produce parts with micron-scale features.

Heat shrink plastics are compatible with the hot embossing method. Heat shrink plastics are normally manufactured by a process in which the plastics are molded or extruded into a shape of choice (such as a tube), then stretched or expanded. Upon heating, the material returns to its original state by contraction. Thus, a type of plastic normally used in heat shrink tubing, such as a polyolefin, could be laid down on a cartridge. Channels could then be added by the hot embossing method. Because the plastic will stretch upon being embossed, it will be poised to contract during microwave microfluidics. The contraction will cause liquid movement.

Another method that could be used to make heat-shrink channels is the wire-imprinting method (Chen & Chen, 2000). In this method, a hot wire is pressed into the plastic, causing deformation and leaving a channel. During microwave microfluidics, the channels would close.

In other embodiments, hollow vesicles or beads can be in thermal proximity to a microwave-susceptible dielectric. Upon microwave heating the dielectric, the hollow vesicle or bead melts, releasing its fluid contents. One type of hollow bead is a wax bead, such as that used in polymerase chain reaction called Hotstart (Stratagene, Inc., La Jolla, Calif., Qiagen Inc.—USA, Valencia, Calif.). Hotstart Beads contain DNA polymerase enzyme solutions used in PCR. If beads such as these were in thermal proximity to a dielectric, then mild microwaves could be used to melt the beads (wax is not by itself susceptible to microwave heating). A related format, also for PCR, is Faststart DNA polymerase (Roche Applied Science, Indianapolis, Ind.). In Faststart DNA polymerase, the enzyme is initially inactive due to a thermo-labile chemical modification. Heat causes scission of the chemical label, and activation of the enzyme. Other types of hollow vesicles are microcapsules (Donbrow, 1991), including wax microspheres (Adeyeye & Price, 1991), lipid micelles (Terabe, 2004), and phospholipid liposomes (Gregoriadis, 1983a, 1983b; Torchilin & Weissig, 2003; Drummond et al., 1999; Duzgunes, 2003, 2004; Ostro, 1987; Basu & Basu, 2002; Kono, 2001; Adeye & Price, 1991). They can be filled with any desired solution. Again, liposomes, being made of lipid coats and being smaller than the wavelength of microwaves, are not by themselves microwave susceptible. However, if positioned near a dielectric, they will rapidly open and release their contents under microwave irradiation.

An additional benefit of vesicles that open upon heating is that they can often be surface-modified with antibodies or other biospecific capture molecules (Drummond et al., 1999; Langer et al., 1999). For example, a liposome could be prepared, which bears on its surface an antibody that captures an analyte (such as a cytokine). A secondary anti-analyte antibody could then be added, which would also bind to the analyte to form an antibody-analyte-antibody "sandwich" on the surface of the liposome. The secondary antibody could be labeled with a chemiluminescent reagent (such as an acridinium ester sold by Assay Designs, Inc., Ann Arbor, Mich.). Acridinium esters require a co-reactant to give a flash of light. The co-reactant solution could be sequestered inside the liposome. Upon directed microwave heating, the liposome would open and the chemiluminescent reagent would react with the acridinium ester to give a flash of light. There are many other examples of the use of two or more reagents to combine to give a signal, such as light emission or color change.

4) Formats of Fluid. The support may have any of a variety of geometries. In most cases, the fluid may be entrapped in a sphere or present in a channel. Also, in most cases, the fluid will be an aqueous liquid used in bioanalytical testing. In the simplest cases, a bolus of liquid is delivered by melting a hollow sphere (e.g. wax or lipid). In more complex cases, channels (or pipes) are organized into networks. Circuits may be formed with numerous intersections and reservoirs. In these cases, channels, capsules, or reservoirs will contract to move liquids by the force of contraction.

There are many practical applications for microfluidics. In many instances, liquids are used on microchips to deliver reagents to one or more bioanalytical testing sites, or to wash a solid phase (Burstoff, 2004; Fitzgerald, 2002; Lesney, 2002; Hansen & Quake, 2003; McDonald et al., 2000; Roper et al., 2003).

Figure 5:
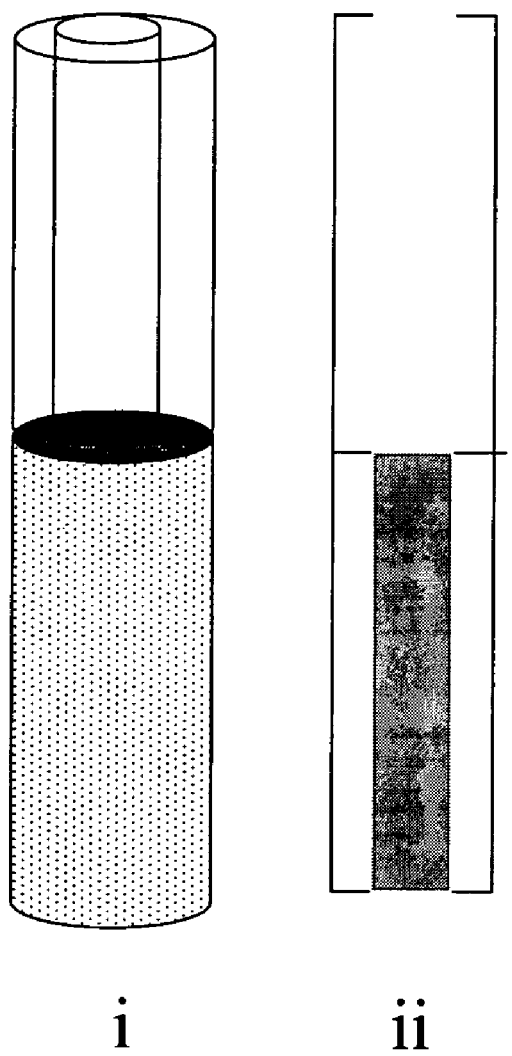
FIG. 5: Isothermal movement of a liquid by microwave microfluidics.

Because of the closeness of fluid to the dielectric/heat-transformable material, it is common for the fluid itself to warm or heat upon microwaving. In many cases, especially in bionanalyses, where biomolecules or cells may require near physiological temperatures, warming of the fluids may be counterproductive. In such cases, it will be beneficial to have an intervening "dummy" fluid in contact with the heat-susceptible material. The intervening liquid will move, and in doing so, move a "downstream" fluid, which does not heat upon microwaving (FIG. 5). The intervening fluid may be the same or different composition as the fluid to be used. For example, if an enzyme solution is to be delivered, the intervening solution and the delivered solution could both be the enzyme solution. Alternatively, the intervening solution could simply be water (or an organic solvent), while the delivered solution could be the enzyme solution.

5) Formats of the Cartridge and Fluidics Capsules. In most cases, microfluidics applications take place on disposable cartridges, often referred to as chips. Of the four essential components of this invention (1) microwave irradiation, is not a part of the cartridge, (2) the microwave-susceptible material, may be a part of the cartridge, and both (3) the heat-susceptible material and (4) the fluid must be a part of the cartridge.

The microwave-susceptible material may or may not be a part of the cartridge. The two critical features of this material are that it must heat well under microwave irradiation, and it must be in thermal proximity to the heat-susceptible material. These criteria can be fulfilled in many ways. First, the microwave-susceptible material may not be integrated into the cartridge, but rather may be permanently integrated into the reaction chamber of the microwave instrument. Similarly, the microwave material may not be integrated into either the cartridge or the instrument, but may be a third unit, which clips or otherwise attaches to the cartridge. In this case, the microwave-susceptible "clip" could be reusable, whereas the cartridge itself would be disposable. Alternatively, the microwave-susceptible may be integrated into the disposable cartridge. In this case, it may either be blended into the heat-susceptible material (such as into a molded polymer) or it may be applied to the cartridge separately. It may for example be painted or screen-printed to the bottom of the cartridge in an appropriate pattern or location. In all cases described, the microwave-susceptible and heat-susceptible materials are considered a composite as long as they are in thermal proximity with each other.

A notable feature of the invention in general, and the cartridge format in specific has to do with the nature of microwave heating. Typical microwave radiation of the frequency of 2.450 GHz found in many devices has a wavelength on the order of 12 centimeters. Very small microfluidics channels and vesicles (sub-centimeter or even sub-micron) do not heat well in microwave radiation for two reasons. One is their small dimensions relative to the wavelength of microwaves render them invisible to microwave heating. The other reason is that they are commonly made from materials, such as plastics, which are not inherently microwave susceptible. Thus, by using a relatively large amount (e.g., painted or screen printed) of microwave-susceptible material, the invention overcomes both hurdles to microwave heating.

Preferred Methods and Compositions of Matter

There are countless ways of practicing the present invention. Some variables include: the microwave frequency and power, the identity of the microwave susceptible material, the identity of the heat-susceptible material, the identity of the fluid to be moved, and the fluidics capsule shape (channel, pipe network, spherical, or other). Pipe networks are collections of channels that are straight, curved, branched, merged or otherwise networked, for example to carry out one or more on-chip functions.

The practical applications of the invention are also highly variable, including countless analytical, preparative, and decontamination functions (Burstoff, 2004; Fitzgerald, 2002; Lesney, 2002; Hansen & Quake, 2003; McDonald et al., 2000; Roper et al., 2003). Described below is a brief overview of preferred parameters for carrying out microwave microfluidics.

1. Cartridge

One highly attractive format for the invention is the single-use disposable cartridge (commonly known as a chip, microchip, biochip, microarray, or macroarray). Chips are typically planar and often made on microscope slides (for example, 1×3 inch rectangles of glass). Microwave microfluidics is highly attractive compared to existing microfluidics technologies because it does not require pumps or external valves, which add cost and complexity.

Two attractive channel formats that have been successfully used are fluid delivery by hollow wax capsules and by heat shrink tubing. These are described in detail the Examples below.

As described above, the dielectric material can be in various formats. Currently the most attractive format is a layer applied beneath the chip. Although the heat-transformable materials (e.g. wax and heat shrink tubing) can be directly coated with a dielectric-containing paint, it is preferable to undercoat the chip beneath the heat-transformable material with a dielectric material, such as BSR-1/SS6M. Another excellent dielectric material is a thick film made from SiC powder mixed with an aqueous polyvinyl acetate (Elmer's Glue-All). The mixture is manually blended to a consistency of toothpaste, applied to the chip by roller or brush, and allowed to air-dry.

Currently, the best way to prepare a wax hollow vesicle on a chip is described below in Example 3. There are two attractive methods of preparing a channel from heat shrink plastic; gluing a piece of heat shrink tubing to a chip (Example 2, below), and gluing a flat piece of heat shrink plastic, such as polyolefin, to a chip and imprinting the plastic with a hot wire or other fine metal device (Example 7, below).

Currently the best channel material is heat shrink tubing, such as the polyolefin tubing described in the Examples 1, 2, 6 and 7. The channels are either used as supplied as tubing by heat shrink tubing manufacturers or by the "wire imprinting" method as described in Example 7.

When using one or more heat shrink tubing channels, it is preferable to use a "spacer" or "dummy" fluid. Because the fluid directly in contact with the portion of the tubing that shrinks will absorb heat and undergo a temperature increase, it is preferable to use a spacer fluid in that portion of the tubing. When the tube diameter shrinks, the spacer fluid will move along the tubing and cause downstream fluid, which does not absorb heat, to move. The downstream liquid is the meaningful fluid (often containing antibodies, enzyme substrates, or other buffered reagents) that is used in the particular application.

2. Instrument

The size and features of the instrument will vary with the practical application. Some feasible types are handheld, portable, and benchtop.

There are numerous feasible designs of instruments. In essence, the instrument must be able to bathe the targeted dielectric in a uniform field of microwave irradiation. Instruments can be made with one or multiple reaction chambers. Instruments can also be different sizes, for example, a benchtop instrument can be made for laboratory use, while a handheld instrument can be made for field use. The reaction chamber can be a waveguide cavity or an oven cavity. An instrument can be as small as the smallest microwave emitters combined with the smallest target reaction chamber. Microwave emitters can be smaller than a house key (e.g., in cell phones). Target reactions can also be smaller than a house key (e.g., a small microarray chip).

Experiments described in the Examples below were performed with a standard kitchen microwave oven. Equivalent or superior results can be expected using purpose-designed microwave-emitting instruments.

3. Applications of the Invention

There are numerous practical applications of microwave fluidics including but not limited to; biochemical research, human and animal medical diagnostics/prognostics, water testing, food pathogen testing, crop testing, and chemical/biological warfare agent testing. In all cases, the invention can be used for preparative, analytical, and/or decontamination functions.

Preparative Applications

Preparation involves physical or chemical reactions in preparation for an analytical reaction. Preparative reactions include solution delivery and mixing for covalent and non-covalent chemical reactions, including macromolecular binding reactions, washing, and analyte amplification reactions.

Preparative (pre-analytical) steps in immunoassays can be facilitated (e.g., on a chip) by microwave microfluidics. An antibody can be delivered to immunoassay reaction zone, allowing it to bind to the analyte. Also, washing solution can be introduced to the reaction zone to remove unbound excess unbound antibody. In addition to solution delivery, the physical force of introduction of solution to a reaction zone can also facilitate mixing and flushing.

Similarly, microwave microfluidics can also be used in nucleic acid assays (e.g., on a chip). Again, solvents can be introduced or mixing, washing, and flushing of a reaction zone can be facilitated.

In addition to those listed above, another preparative step in nucleic acid analysis can be facilitated using this invention. Polymerase chain reaction (PCR), used to amplify the number of copies of an analyte nucleic acid strand, can also be improved by the invention. A temperature-dependent aspect of PCR that is now commonly practiced is the sudden introduction of reagents that are entrapped in hollow wax spheres (Newton & Graham, 1994; McPherson & Moller, 2000). The idea is that reagents can be physically isolated by a wax partition until needed. Commercial wax bead products include Taq Bead™ Hot Start Polymerase (enzyme compartmentalization, Promega), StartaSphere™ beads (magnesium compartmentalization, Stratagene). An alternative is to inactivate a reagent with an antibody, which heat denatures. JumpStart™ Taq DNA polymerase (Sigma) is an example of this. The DNA polymerase is temporarily inactivated by a specific antibody, which dissociates upon heating. In microwave microfluidics, the wax or other coating agent can be located in thermal proximity to a microwave-targeted dielectric, and can melt/dissociate to release the desired reagent upon microwaving. The transmission of heat from the dielectric to the coating agent might be especially critical if the coating is made from a microwave-transparent medium, such as paraffin wax (Surrmeijer et al., 1990), that would not heat directly by microwaving. As described below in Example 4 (and illustrated in FIG. 4), we found that the presence of the dielectric is critical to efficiently melt a wax capsule using microwaves.

Analytical Applications

An analytical signal-generating chemical reaction can be triggered by microwave microfluidics. In this application, an analyte is detected by the microwave microfluidics introduction of a solution, which causes a chemical reaction leading to a detectable signal. Examples of signal-generating solutions include; an enzyme or enzyme substrate to trigger color change, a chemiluminescent reagent or oxidant to trigger light emission, or introduction of an optimal buffer for detection of a fluorescent label. Detailed descriptions of two such analytical applications can be found in Examples 2 and 8.

Three common types of analytical uses for microfluidics (and this invention) are detection and measurement of proteins (immunoassays), nucleic acids (DNA and RNA testing), and clinical chemistry analytes (glucose, cholesterol, and other classical tests). All of these may require a signal generating or enhancing introduction of fluids. In all cases, a reactant solution can be delivered to the analyte using microfluidics.

Decontamination Applications.

Specimens often contain hazardous components that require safe post-analysis disposal. Specimens used in medical or food testing may contain infectious agents. Environmental specimens collected in biological or chemical warfare testing may contain infectious agents or toxic chemicals.

If a test has been conducted on a chip, there is a danger that the chip may be contaminated and it will require safe disposal. The conventional method of disposal is to save the chip until it can be incinerated. Saving a contaminated chip may be dangerous, especially if the chip is contaminated during field-testing and it must be carried for a great distance over a prolonged period of time before disposal.

Microwave microfluidics can be used to deliver a disinfecting or chemical inactivating solution to a specimen after the specimen has been analyzed. The solution may contain bleach, isopropyl alcohol, acid, or other appropriate solution.

EXAMPLES

Example 1

Heat-Shrink Tubing Coated with Dielectric

Figure 2A:
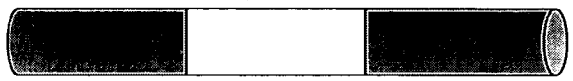
FIG. 2: Channel microwave microfluidics.
Figure 2A:
Figure 2A:
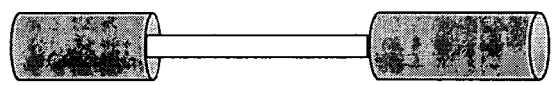

Short lengths (approximately 3-5 cm) of polyolefin-based heat shrink tubing (22-18 AWG, Gardner Bender, Milwaukee, Wis.) were partially painted with dielectric paint. The paint was a mixture of $BaTiO_3$ powder and polyvinyl acetate aqueous adhesive (Elmer's Glue-All®) blended to a consistency of common toothpaste. The middle third segment of tubing was painted entirely around and the two outside thirds were left bare. After the paint had dried, the tubing was placed in a microwave oven (600 W) and microwaved for 30 seconds. The diameter painted middle segment of the tubing constricted by about 50%, while the outside segments remained the same diameter (FIG. 2A).

In another experiment, tubing was wrapped with a piece of carbon-based adhesive-backed dielectric (BSR-1/SS6M, Emerson & Cuming). This dielectric was purchased in silicone-based thin (0.01") sheets, which were cut with a razor blade to the appropriate dimensions. As above, the dielectric-wrapped tubing was microwaved for 30 seconds. The diameter of the tubing that was wrapped with dielectric shrunk by about 50%, while unwrapped tubing remained unchanged.

Figure 2B:
Figure 2B:
Figure 2B:
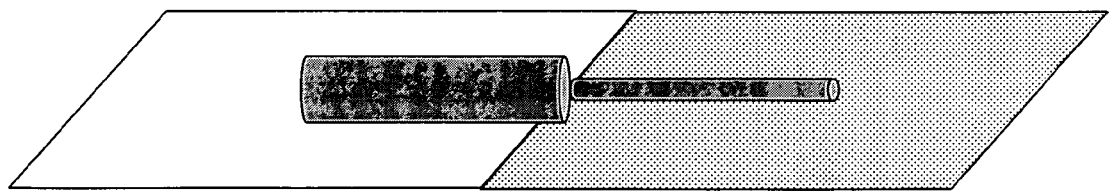

In another experiment, a piece of BSR-1/SS6M dielectric (approximately 1"×1.5") was affixed to one-half of the underside of a standard 1"×3" microscope slide. The other half of the slide (about 1"×1.5") was left bare. A piece of heat shrink tubing (Gardner Bender, ⅛" diameter by about 2" length, was placed lengthwise on top (the glass side) of the slide, spanning both dielectric undercoated and plain halves of the slide. The slide and tubing were placed in a microwave oven (600 W) and microwaved for 30 seconds. The tubing over the dielectric undercoated part of the slide contracted by about 50% (diameter), while the portion of the tubing over the bare glass did not appear to change at all (FIG. 2B).

These experiments demonstrated that a composite of heat shrink polymer and dielectric responds readily to microwaves, but the heat shrink material alone is not affected.

Example 2

Microwave Microfluidics using Heat Shrink Tubing-Dielectric Composite

Example 1 showed that a composite of microwave-active material and heat shrink polymer responded rapidly and markedly to mild microwave irradiation. Microwaving the composite caused constriction of the heat shrink tubing. The composites can be considered "smart materials". We next tested the composites to determine if they could be used to move liquids, as a result of the force of contraction observed upon microwaving.

Figure 3:
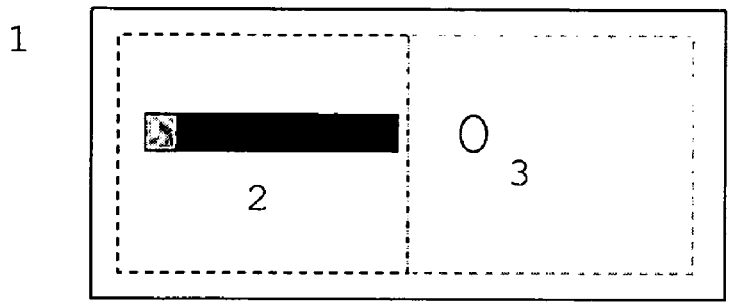
FIG. 3: Directed microwave ejection of liquids from a channel.
Figure 3:
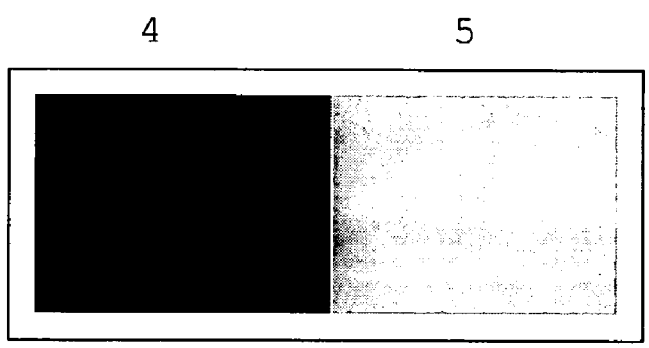

A microfluidic chip (FIG. 3) was assembled starting with a nitrocellulose membrane-coated microscope slide. Underneath the slide, two pieces of microwave-active adhesive dielectric material were affixed to the glass—MCS/SS6M (0.04" thick) and BSR-1/SS6M (0.01" thick)(Emerson & Cuming). On top of the slide (the nitrocellulose side) was glued a length of heat shrink tubing (311640, Squire Electronics). The tubing had been filled with an oxidant solution (62.5 mM $NaBO_3$, 100 mM $NaHCO_3$, 0.0176 g/L $CoCl_2$, pH 7.6) and plugged at one end. Near, but not in contact with, the open end of the tubing was then spotted 0.5 µL of chemiluminescent reagent APS-5 (Lumigen, Inc.). APS-5 emits a flash of light when mixed with oxidant and heated. The spot was allowed to dry. X-ray film was then placed on top of the slide to record any light emission (HyperFilm ECL, Amersham).

The microfluidic chip was placed in a 600 W microwave oven and microwaved for 30 seconds in the dark. Upon removal, it could be seen that heating the MCS dielectric caused the tubing to shrink, which caused the liquid oxidant to be released from the open end. Development of the X-ray film showed that the oxidant had indeed left the tubing, mixed with the chemiluminescent reagent, and caused light emission (the reaction was initiated by the microwave-heated. BSR-1 dielectric).

This experiment was repeated twice with the same results. These data demonstrated for the first time that microwave microfluidics could move liquids from storage to a desired location to perform a task.

Example 3

Preparation of Dielectric/Wax Composites

Examples 1 and 2 describe tube or channel microfluidics. Another embodiment is vesicle microwave microfluidics. Here, vesicles enclose a fluid of choice. The vesicles are designed to melt upon mild microwave irradiation. This is accomplished by using a composite containing a microwave-active material and a material with a melting point that is between typical room temperature (20° C.) and the boiling point of water (100° C.).

Figure 4:
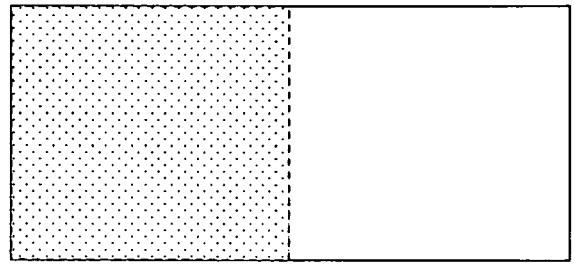
FIG. 4: Vesicle microwave microfluidics.
Figure 4:
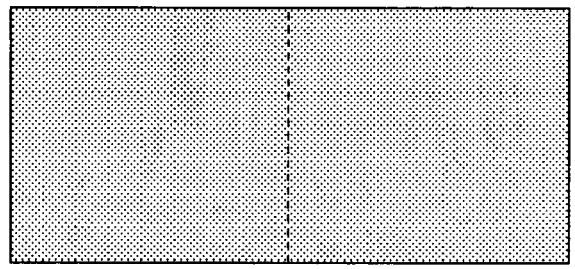
Figure 4:
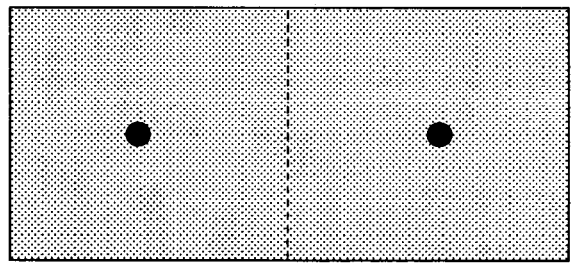
Figure 4:
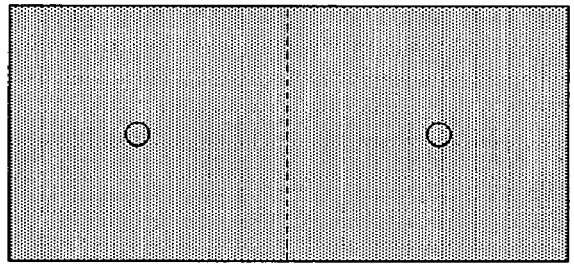
Figure 4:
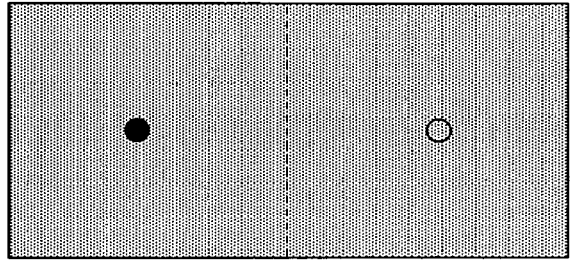

A standard glass microscope slide (1"×3") was undercoated with a piece of dielectric (adhesive-backed BSR-1, Emerson & Cuming, Randolph, Mass.)(FIG. 4). Wax was chosen as an encapsulating material because of its low melting point (approx. 55° C.) and its resistance to direct microwave heating. Shavings of paraffin wax were placed on the slide and the slide was microwaved until the wax melted. Excess wax was decanted from the slide leaving a thin film of wax, which rapidly hardened. The dielectric was removed from one-half of the slide, leaving a "dielectric side" and a "plain side" to the wax-coated slide. On top of each side was pipetted one spot of 10.0 µL of 10.0 mM $KMnO_4$ in water. This compound was used as a purple colored indicator. The aqueous $KMnO_4$ formed excellent, nearly spherical beads on the waxed slide. The $KMnO_4$ beads were encapsulated with wax in the next step. Molten wax was dripped onto the $KMnO_4$ beads. The melted wax coated the aqueous beads with a thin layer that rapidly hardened to completely enclose the liquid.

Example 4

Releasing Liquid from Dielectric/Wax Composite Capsules

The slide described in Example 3 was tested to determine if, upon microwaving, the underlying dielectric aided in wax melting and liquid liberation (FIG. 4). Both sides (the dielectric side and the plain side) were individually washed with 3.0 mL of water, which was saved to determine if any $KMnO_4$ was leaking. The slide was then microwaved for 40 seconds. It was visibly observed that the wax had melted on the dielectric side (and $KMnO_4$ was liberated), but not on the plain side. Each side was quickly washed with 3.0 mL of water, which was saved to measure $KMnO_4$ liberation. Three of the washes—the pre-microwave washes and the post-microwave plain wash—were clear, while the fourth wash, the post-microwave dielectric side was pink.

The four washes were measured in a spectrophotometer (Hitachi 3010) at 545 nm where $KMnO4$ absorbs strongly. The following absorbances were recorded; (1) pre-microwave dielectric side, 0.000, (2) pre-microwave plain side, −0.002, (3) post-microwave dielectric side, 0.041, (4) post-microwave plain side, −0.002.

These data clearly show that, although low volume liquids cannot be easily liberated from wax capsules by microwaves alone, the liquids readily emerge when the wax capsules are in thermal proximity to a microwave-susceptible material.

Example 5

Liposome Microwave Microfluidic Capsules

Polymer or lipid vesicles such as liposomes can hold liquids and are heat-transformable (amenable phase transition temperatures). Provided here is an example of how liposomes could be used as heat-sensitive reagent-releasing containers.

There are numerous liposome preparation methods. In the use of liposomes as storage capsules, as described herein, it is advantageous to form liposomes with large diameters (500 Å to several microns). This can be done using a single type of phospholipid, such as egg white lecithin. Lipid is dissolved in organic solvent, such as chloroform, in a round-bottom flask, along with glass or Teflon beads (1-2 mm). The flask is then rotary evaporated to leave a thin lipid film in the flask. The lipid film is then hydrated by agitation (enhanced by the added beads) with the aqueous medium to be entrapped in the liposomes. The resulting liposomes are then washed by centrifugation and resuspension in aqueous solution (Gregoriadis, 1983a; Torchilin & Weissig, 2004).

Liposomes containing reagent can be prepared as described above with the chemiluminescent reagent, CDP-Star (Applied Biosystems, Inc.). CDP-Star (with Nitro II enhancer) is obtained and used in a ready-to-use solution (0.25 mM).

A layer of washed CDP-Star liposomes are deposited on a BSR-1 dielectric-undercoated (Emerson & Cuming, Randolph, Mass.) FAST Slide (Schleicher & Schuell, Keene, N.H.). FAST slides are commercially available nitrocellulose-coated glass microscope slides used for immunoassays.

An immunoassay for TNFα is carried out on the chip as described in the FAST Slide manufacturer instructions, using a human TNFα DuoSet immunoassay antibody reagent kit and human TNFα standard (R&D Systems, Minneapolis, Minn.). The immunoassay label used is horseradish peroxidase enzyme.

Signal generation is carried out without having to add chemiluminescent reagent, since the reagent is previously added to the chip entrapped in liposomes. The slide is gently heated in a microwave oven to the phase transition temperature of the liposomes. The dielectric absorbs microwave energy, converts it to heat, and the heat causes chemiluminescent reagent to be released. Released CDP-Star reacts with the horseradish peroxidase label, and resultant light emission is captured on X-ray film. The analyte TNFα can thus be detected on a chip.

Example 6

Isothermic Movement of Liquids in a Dielectric Channel

When microwave microfluidic channels heat and shrink the fluid contents of the internal lumen may also warm. This is undesirable in applications (e.g. medical or biochemical analyses) because the reagent solutions often contain fragile or otherwise heat-sensitive solutes such as antibodies. Thus, it is advantageous to use a "spacer" fluid, which is in contact with a heat shrink channel. The spacer fluid moves when the channel contracts, but does not enter the actual analytical reaction zone. This is demonstrated in the representation in FIG. 5. On the left (i), a heat shrink channel is coated with dielectric at the bottom, but not at the top. Inside the channel (ii in FIG. 5) is a "spacer" fluid at the bottom and the analytically relevant fluid at the top. The identity of the spacer fluid is largely irrelevant (it may an aqueous or organic solution). The "analytical" fluid will have necessary solutes for a given reaction (antibodies, salts, buffers, enzymes, etc.).

Upon microwaving the dielectric sheath will heat, causing the tubing to contract. The spacer fluid will move (upward in FIG. 5) and displace the analytical fluid, which will move (also upward in FIG. 5) into a desired reaction zone.

Example 7

Wire-Imprinting Heat Shrink Plastic to form a Channel

One method to form heat-susceptible channels is by the wire-imprinting method (Chen & Chen, 2000). Here is described the application of this method to the formation of channels for microwave microfluidics.

A piece of polyolefin tubing (3.2×105 mm, 22-18 AWG, Gardner Bender, Milwaukee, Wis.) was spilt in half lengthwise. A square tip of a stainless steel laboratory spatula (9 mm×1 mm) was heated by contact with a conventional hotplate. The tip was then pressed against a piece of polyolefin described above, resulting in a well-defined channel imprint (1 mm wide×9 mm long). This procedure was repeated along the length of the polyolefin to give a series of well-defined short depressions. Each depression was approximately 1 mm deep. This showed that microfluidics channels can be formed in heat shrink plastic by the wire-imprinting method.

An experiment was then carried out to test whether the wire-imprinted channels could be made to contract upon heating. One half (1×1.5 cm) of a microscope slide (1×3 cm) was undercoated with BSR-1/SS6M dielectric (Emerson & Cuming). The wire-imprinted polyolefin was affixed flat to the surface of the slide using a rubber band. One channel was over bare glass (no dielectric undercoating) and two channels were positioned over the dielectric. The chip was placed in a 600 W microwave oven and microwave irradiated for 30 seconds. The slide was removed and the polyolefin was visually inspected. It was found that microwaving had no visible effect on the channel over bare glass, but the channels over the dielectric were completely or almost completely closed. This demonstrates that the wire imprinting method can be used to form microchannels which contract in microwave microfluidics.

Example 8

Immunoassay on a Microwave Microfluidics Cartridge

This Example illustrates how an immunoassay can be carried out on a chip using microwave microfluidics. One skilled in the art could apply this Example into other types of solid phase assays including DNA and mRNA tests, and receptor-ligand binding tests.

Figure 6:
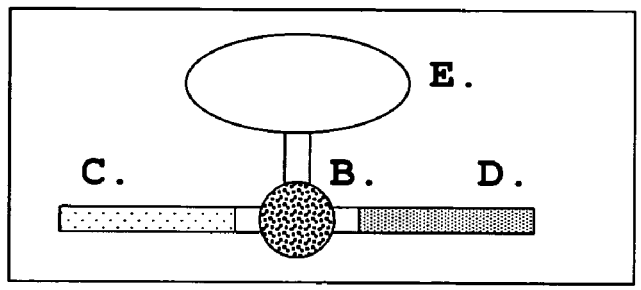
FIG. 6: Microwave microfluidics chip designed for an immunoassay.
Figure 6:
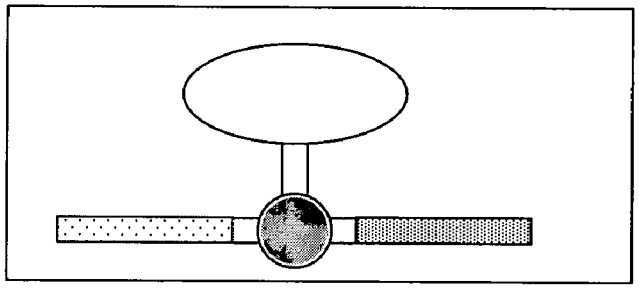
Figure 6:
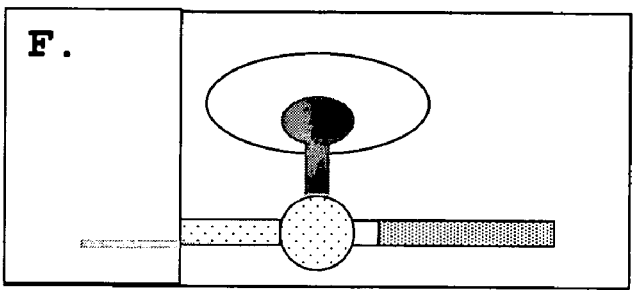
Figure 6:
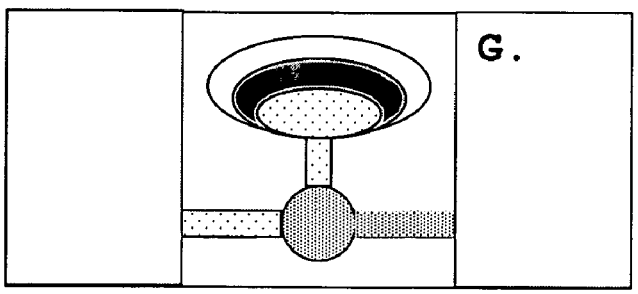

FIG. 6 illustrates a chip at various steps of the immunoassay. Other chip designs are also possible. The chip consists of (FIG. 6, panel 1); (A) A rectangular piece of glass (1×3 inches) onto which are etched deep channels for the liquid conduits and reaction zone (B, C, D, E). (B) A reaction zone (B) made of cast porous nitrocellulose (similar to FAST slides, Schleicher & Schuell Biosciences, Keene, N.H.) on which the immunoassay takes place. An anti-human TNFα capture antibody is bound to the nitrocellulose by conventional adsorption method (DuoSet, R&D Systems, Minneapolis, Minn.). The nitrocellulose pad is also blocked to prevent non-specific binding (Schleicher & Schuell Biosciences, Keene, N.H.). (C) Leading to the nitrocellulose bed is a heat shrink tube (3/64" diameter) (Squires Electronics, Inc., Cornelius, Oreg.) that is glued into the etched channel in the glass slide. The tube contains a buffered solution of horseradish peroxidase-labeled anti-TNFα secondary antibody (Amersham Biosciences & DuoSet Antibody Kit, R&D Systems). The tube is plugged on the end opposite the reaction zone to prevent liquid from escaping in the wrong direction. (D) Also leading to the nitrocellulose bed is a second heat shrink tube (3/64" diameter) (Squires Electronics, Inc., Cornelius, Oreg.) that is glued into the etched channel in the glass slide. This tube (D) contains CDP-Star chemiluminescent reagent (with Nitro II Enhancer, purchased as a ready-to-use solution, Applied Biosystems). Tube (D) is also plugged on the end opposite the reaction zone to prevent liquid from escaping in the wrong direction. (E) Leading away from the reaction zone is a bare (i.e., not made of heat shrink material) waste channel that leads into a waste reservoir.

The assay is carried out by the following steps:

1) Ten microliters of a buffered solution of 500 pg/mL human TNFα (standard, from R&D Systems) is added to the nitrocellulose pad on the chip using a pipette (as shown in FIG. 6, panel 2). The analyte TNFα is allowed to bind to the capture antibody for 2 hours at room temperature. Care is taken so that there is no contact between the analyte solution and the "on-chip" solutions in (C) and (D).

2) The analyte solution is removed and the nitrocellulose pad is washed four times for 10 minutes each using PBS/Tween (1 wash) and PBS (3 washes) buffers.

3) A 1"×3/4" piece of adhesive-backed dielectric (BSR-1/SS6M, 0.01" thick) is added to the back of the chip ((F) in FIG. 6, panel 3). The chip is then microwaved for 60 seconds using 600 W of power. Microwaving causes the heat shrink tubing in thermal proximity to the dielectric to contract (C), expelling the contents onto the nitrocellulose pad (FIG. 6, panel 3). Notably, the dielectric is in thermal proximity with only a portion of tubing (C), such that the reagent solution that is expelled from (C) is not warmed by the dielectric.

4) The expelled contents of (C), which include anti-TNFα secondary antibody-horseradish peroxidase, are incubated on the nitrocellulose pad for two hours at room temperature to allow the antibody to bind to analyte TNFα.

5) The expelled contents of (C) are removed and the nitrocellulose pad is washed four times for 10 minutes each using PBS/Tween (1 wash) and PBS (3 washes) buffers.

6) A 1"×3/4" piece of adhesive-backed dielectric (BSR-1/SS6M, 0.01" thick) is added to the back of the chip (G in FIG. 6, panel 4). The chip is then microwaved for 60 seconds using 600 W of power. Microwaving causes the heat shrink tubing (D) in thermal proximity to the dielectric to contract, expelling the contents onto the nitrocellulose pad (FIG. 6, panel 4). Notably, the dielectric is only in thermal proximity with a portion of tubing (D), such that the reagent solution that is expelled from (D) is not warmed by the dielectric.

7) The expelled contents of (D) include the chemiluminescent enzyme substrate of horseradish peroxidase, CDP-Star. When CDP-Star reacts with horseradish peroxidase, light is emitted, signaling the presence of horseradish peroxidase (and hence, in this Example, the analyte TNFα). Light emitted signaling the presence and concentration of the analyte TNFα is captured on autoradiography film (Hyperfilm ECL, Amersham). Film exposure is for a period of time suitable for detection as recommended by the film manufacturer. The film is developed and the analyte is detected as a dark spot on the film.

REFERENCES

Below is a list of publications cited herein:

Adeyeye, C. M. & Price, J. C. (1991) Pharm. Res. 8, 1377-1383. ASTM Committee E20 on Temperature Measurement (1993) ASTM, Philadelphia.
Basu, S. C. & Basu, M. (2002) Liposome Methods and Protocols, Humana Press, Totowa, N.J., pp. 3-16.
Becker, H. & Gartner, C. (2000) Electrophoresis 21, 12-26.
Beebe, D. J., Mensing, G. A., Q& Walker, G. M. (2002) Annu. Rev. Biomed. Eng. 4, 261-286.
Boon, M. E. & Kok, L. P. (1989) in Microwave Cookbook of Pathology, Coulomb Press, Leiden.
Bose, A. K. et al. (1997) CHEMTECH 27(9), 18-25.
Bradley, D. (2001) Modern Drug Discovery 4(8), 32-36.
Bram, G., Loupy, A., Majdoub, M., and Petit, A. (1991) Chem. Ind. 396.
Burtsoff, C. (2004) Modern Drug Discovery 7, 55-56.
Chen, Y.-H. & Chen, S.-H. (2000) Electrophoresis 21, 165-170.
Donbrow, M. (1991) Microcapsules and Nanoparticles in Medicine and Pharmacy, CRC Press, Boca Raton, Fla., pp. 1-14.
Drummond, D. C., Myer, O., Hong, K., Kirpotin, D. B., and Papahadjopoulos, D. (1999) Pharm. Rev. 51, 691-743.
Duzgunes, N. (2003) Methods Enzymol. 367, 99-110.
Duzgunes, N. (2004) Methods Enzymol. 373, 260-277.
Ewart, T. G. & Gavin, G. T. (1999) Nanoparticles Biosensor, U.S. Pat. No. 5,922,537.
Fermer, C., Nilsson, P., & Larhead, M. (2003) Eur. J. Pharm. Sci. 18, 129-132.
Fitzgerald, D. A. (2002) The Scientist 16, 40-42.
Fong, R. B., Ding, Z., Hoffmann, A. S., & Stayton, P. S. (2002) 79, 271-276.
Gabriel, C., Gabriel, S., Grant, E. H., Halstead, B. S. J., Mingos, D. M. P. (1998) Chem. Soc. Rev. 27, 213-224.
Gregoriadis, G. (1983a) Liposome Technology Volume I. Preparation of Liposomes. CRC Press, Boca Raton, Fla., pp. 1-18.
Gregoriadis, G. (1983b) Liposome Technology Volume III. Targeted Drug Delivery and Biological Interaction. CRC Press, Boca Raton, Fla., pp. 137-155.
Hansen, C. & Quake, S. R. (2003) Curr. Opin. Struct. Biol. 13, 538-544.
Hjerpe, A., Boon, M. E., & Kok, L. P. (1988) 20, 388-396.
Hoffman, A. S. (2000) Clin. Chem. 46, 1478-1486.
Huhmer, A. F. R. and Landers, J. P (2000) Anal. Chem. 72, 5507-5512.
Jain, S., Sharma, S., & Gupta, M. N. (2002) Anal. Biochem. 311, 84-86.
Jeong, B. & Gutowska, A. (2002) Trends Biotechnol. 20, 305-311.
Kok, L. P. & Boon, M. E. (1990) Histochem. J. 22, 381-388.
Kono, K. (2001) Adv. Drug Deliv. Rev. 53, 307-319.
Kreider, K. G. (1989) Thin Film Thermocouples For High Temperature Measurement. NIST, Springfield, Va.
Langer, R. S. & Chen, H. (1999) U.S. Pat. No. 6,004,534.
Laslo, T. S. (1980) The Physics Teacher, November, 570-579.
Lesney, M. S. (2002) Modern Drug Discovery, 5, 37-41.
Leong, A. S.-Y. & Milios, J. (1986) J. Pathol. 148, 183-187.
Lew, A., Krutzik, P. O., Hart, M. E., & Chamberlain, A. R. (2002) J. Comb. Chem. 4, 95-105.

McDonald, J. C., Duffy, D. C., Anderson, J. R., Chui, D. T., Wu, H., Schueller, O. J. A., & Whitesides, G. M. (2000) Electrophoresis 21, 27-40.

McPherson, M. J. & Moller, S. G. (2000) PCR. Bios Scientific Publishers, Oxford, UK.

Mingos, D M P & Baghurst, D R (1991) Chem. Soc. Rev. 20, 1-47.

Morrison, D. R. & Mosier, B. (2000) U.S. Pat. No. 6,099,864.

Nesatyy, V. J., Dacanay, A., Kelly, J. F., & Ross, N. W. (2002) Rapid Commun. Mass Spectrom. 16, 272-280.

Newton, C. R. & Graham, A. (1994) PCR. Springer-Verlag, New York.

Ostro, M. J. (1987) Liposomes. From Biophysics to Therapeutics. Marcel Dekker, New York, pp. 297-298.

Roper, M. G., Shackman, J. G., Dahlgren, G. M., & Kennedy, R. T. (2003) 75, 4711-4717.

Roy, I. & Gupta, M. N. (2003) Chemistry and Biology 10, 1161-1171.

Slap, S. E. (2003) Am. Biotechnol. Laboratory, November, 40.

Slyanev, M. N. (2001) Anal. Chem. 73, 4037-4044.

Surrmeijer, A. J. H., Boon, M. E., & Kok, L. P. (1990) Histochem. J. 22, 341-346.

Terabe, S. (2004) Anal. Chem. 76, 240A-246A.

Torchilin, V. & Weissig, V. (2004) Liposomes. A Practical Approach. $2^{nd}$ Ed., Oxford Univ. Press, Oxford UK., pp. 3-29.

Van den Brink, W. J., Zijlmans, H. J. M. A. A., Kok, L. P., Bolhuis, P., Volers, H. H., Boon, M. E., & Houthoff, H. J. (1990) Histochem. J. 22, 327-334.

Van de Kant, H. I. J., Boon, M. E., & de Rooij, D. G. (1988) Histochem. J. 20, 3350340.

Wathey, B., Tierney, J., Lidström, P., & Westman, J. (2002) Drug Discovery Today 7, 373-380.

Yang, P. et al. (1998) Science 282, 2244.

Zlotorzynski, A. Crit. Rev. Anal. Chem. (1995) 25, 43.

All publications and patents mentioned in this specification are herein incorporated by reference to the same extent as if each individual publication or patent application was specifically and individually indicated to be incorporated by reference in the entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for moving a fluid or object comprising;
   (a) providing a composite comprised of at least a first material, and a second material that is in thermal proximity to the first material, wherein the first material increases in temperature upon absorption of electromagnetic radiation and the second material melts or changes shape upon heat transfer;
   (b) placing the composite in contact with said fluid or object;
   (c) thereafter applying electromagnetic radiation to the composite allowing said first material to undergo a temperature change sufficient to cause said second material to melt or change shape, wherein such melting or changing shape of the second material causes a change of position of the second material thereby causing movement of said fluid or object, wherein the wavelength of said applied electromagnetic radiation is between 5 cm and 100 m.

2. The method of claim 1, wherein the change of position of the second material applies a change of force on the fluid or object thereby causing said movement thereof.

3. The method of claim 1, wherein the change of position of the second material allows a force applied to the fluid or object to cause said movement thereof.

4. The method of claim 3, wherein the applied force is gravity and the composite is applying a force equal and opposite to the force of gravity until the second material melts or changes shape, such that the fluid or object thereby moves under the force of gravity.

5. The method of claim 3, wherein the applied force is external and the composite is applying a force equal and opposite to the external force until the second material melts or changes shape, such that the fluid or object thereby moves in response to the external force.

6. The method of claim 5, wherein the external force is selected from the group consisting of hydraulic, pneumatic, spring, vacuum, capillary, and wicking.

7. The method of claim 1, wherein the composite is an elongated substrate and the step of applying electromagnetic radiation to the composite is in an area on the substrate proximal to the fluid or object to cause movement of the fluid object from a first position on the substrate to a second position on the substrate.

8. The method of claim 1, wherein said first material contains one or more material(s) selected from the group consisting of carbon, clay, $BaTiO_3$, inorganic titanates, inorganic niobates, ferroelectric polymers, $Al_2O_3$—$Fe_3O_4$, $Fe_3O_4$, organic polymers, aluminum-epoxy composites, silicon oxides, $LaCoO_3$, $LaSrO_3$, $LaMnO_3$, $LaFeO_3$, SiC, AlN, ZnO, MgO—SiC, $Al_2O_3$, AlN—SiC, CrB, $Fe_2B$, $SiC/SiO_2$, alumina, mullite, zircon, MgO, $Si_3N_4$, Si, Mg, FeSi, $Cr_2O_3$, MgO, $MnO_2$, NiO, calcium aluminate, ITO, Nb, TaC, SiC, $MoSi_2$, Cu, Fe, $ZrO_2$, $Y_2O_3$, zirconium oxynitrate, aluminum nitrate, yttrium nitrate, and ferrites.

9. The method of claim 1, wherein said second material contains one or more material(s) selected from the group consisting of polyolefin, fluoropolymer, chlorinated polyolefin, highly flexible elastomer, wax, lipid, and phospholipid.

10. The method of claim 1, wherein the fluid is an aqueous or organic liquid.

11. The method of claim 1, wherein said temperature change is between 1° C. and 200° C.

12. The method of claim 1, wherein the direction of the fluid movement is linear, branched, expanding planar, or expanding spherical.

13. The method of claim 1, wherein said fluid movement initiates a chemical reaction involving one or more solutes of said fluid.

14. The method of claim 1, wherein said fluid movement initiates a chemical reaction involving one or more solutes in said fluid, and in which the extent or rate of said chemical reaction can be measured.

15. The method of claim 1, wherein the second material does not substantially increase in temperature by absorbing electromagnetic radiation.

* * * * *